United States Patent
Ramamoorthy et al.

(10) Patent No.: US 11,813,358 B2
(45) Date of Patent: Nov. 14, 2023

(54) LIPID NANODISC FORMATION BY POLYMERS HAVING A PENDANT HYDROPHOBIC GROUP

(71) Applicant: THE REGENTS OF THE UNIVERSITY OF MICHIGAN, Ann Arbor, MI (US)

(72) Inventors: Ayyalusamy Ramamoorthy, Ann Arbor, MI (US); Thirupathi Ravula, Ann Arbor, MI (US); Nathaniel Z. Hardin, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 123 days.

(21) Appl. No.: 16/893,772

(22) Filed: Jun. 5, 2020

(65) Prior Publication Data
US 2020/0383918 A1    Dec. 10, 2020

Related U.S. Application Data

(60) Provisional application No. 62/858,724, filed on Jun. 7, 2019.

(51) Int. Cl.
*A61K 9/127* (2006.01)
*C08F 220/18* (2006.01)
(Continued)

(52) U.S. Cl.
CPC .......... *A61K 9/1278* (2013.01); *A61K 9/1273* (2013.01); *C08F 8/02* (2013.01); *C08F 8/32* (2013.01); *C08F 220/1804* (2020.02)

(58) Field of Classification Search
CPC .. A61K 9/127; A61K 9/1278; C08F 220/1804
See application file for complete search history.

(56) References Cited

U.S. PATENT DOCUMENTS 3,888,945 A    6/1975 Arndt et al.
7,452,551 B1    11/2008 Unger et al.
(Continued)

FOREIGN PATENT DOCUMENTS

CN    103665989 A    3/2014
DE    2136585 A1    11/1972
(Continued)

OTHER PUBLICATIONS

Thirupathi Ravula, Sudheer Kumar Ramadugu, Giacomo Di Mauro, and Ayyalusamy Ramamoorthy. "Bioinspired, Size-Tunable Self-Assembly of Polymer-Lipid Bilayer Nanodiscs." Angewandte Chemie International Edition, vol. 56, 2017, pp. 11466-11470. (Year: 2017).*

(Continued)

*Primary Examiner* — Isaac Shomer
(74) *Attorney, Agent, or Firm* — MARSHALL, GERSTEIN & BORUN LLP

(57) ABSTRACT

The disclosure generally relates to lipid nanodiscs, in particular to lipid nanodiscs formed from polymers. A lipid nanodisc according to the disclosure includes a lipid bilayer having a first hydrophilic face and a second hydrophilic face opposing the first hydrophilic face, and a hydrophobic edge between the opposing hydrophilic faces, and a polymer encircling the hydrophobic edge of the lipid bilayer. The polymer includes a first monomeric unit having a pendant hydrophobic group and a second monomeric unit having a backbone hydrophilic group. Methods of making and characterizing the lipid nanodiscs are also disclosed.

24 Claims, 11 Drawing Sheets

(51) Int. Cl.
   *C08F 8/32* (2006.01)
   *C08F 8/02* (2006.01)

(56) References Cited

U.S. PATENT DOCUMENTS

| | | | |
|---|---|---|---|
| 8,088,400 | B2 | 1/2012 | Toreki et al. |
| 11,092,605 | B2* | 8/2021 | Ramamoorthy ....... G01N 21/35 |
| 2009/0117164 | A1 | 5/2009 | Toreki et al. |
| 2012/0128967 | A1 | 5/2012 | Belcher, Jr. et al. |
| 2019/0346464 | A1* | 11/2019 | Ramamoorthy ....... G01N 33/92 |

FOREIGN PATENT DOCUMENTS

| | | |
|---|---|---|
| DE | 10010851 A1 | 9/2000 |
| JP | H05092129 A | 4/1993 |
| JP | H08159998 A | 6/1996 |
| JP | H11209417 A | 8/1999 |
| JP | 2004-001240 A | 1/2004 |
| JP | 4926681 B2 | 5/2012 |
| JP | 2012-136464 A | 7/2012 |
| JP | 2012-232287 A | 11/2012 |
| JP | 2013-020111 A | 1/2013 |
| JP | 2014-064988 A | 4/2014 |
| JP | 2014-134573 A | 7/2014 |
| KR | 2011133264 | 12/2011 |
| WO | WO-2005/012636 A1 | 2/2005 |
| WO | WO-2007/024973 A1 | 3/2007 |
| WO | WO-2008/081995 A1 | 7/2008 |
| WO | WO-2009/022559 A1 | 2/2009 |

OTHER PUBLICATIONS

Kazuma Yasuhara, Jin Arakida, Thirupathi Ravula, Sudheer Kumar Ramadugu, Bikash Sahoo, Jun-ichi Kikuchi, and Ayyalusamy Ramamoorthy. "Spontaneous Lipid Nanodisc Fomation by Amphiphilic Polymethacrylate Copolymers." Journal of the American Chemical Society, vol. 139, 2017, pp. 18657-18663. (Year: 2017).*

Kazuma Yasuhara et al. "Spontaneous Lipid Nanodisc Fomation by Amphiphilic Polymethacrylate Copolymers." Journal of the American Chemical Society, vol. 139, 2017, pp. 18657-18663. (Year: 2017).*

Zoe Stroud, Stephen C.L. Hall, Tim R. Dafforn. "Purification of membrane proteins free from conventional detergents: SMA, new polymers, new opportunities and new insights." Methods, vol. 147, 2018, pp. 106-117. (Year: 2018).*

Elena N. Danilovtseva, Uma Maheswari Krishnan, Viktor A. Pal'shin and Vadim V. Annenkov. "Polymeric Amines and Ampholytes Derived from Poly(acryloyl chloride): Synthesis, Influence on Silicic Acid Condensation and Interaction with Nucleic Acid." Polymers, vol. 9, 2017, pp. 1-18. (Year: 2017).*

Wou.edu. https://wou.edu/chemistry/files/2017/04/hbonding-cooh-and-ester.png accessed Dec. 9, 2022, 1 printed page. (Year: 2022).*

Pslc.ws. https://www.pslc.ws/macrog/kidsmac/pendant.htm accessed Dec. 9, 2022, pp. 1-2. (Year: 2022).*

LibreTexts. https://batch.libretexts.org/print/url=https://eng.libretexts.org/Bookshelves/Materials_Science/Supplemental_Modules_(Materials_Science)/Polymer_Chemistry/Polymer_Chemistry%3A_Chemical_Composition/Polymer_Chemistry%3A_Pendant_Groups.pdf accessed Dec. 9, 2022, 1 page. (Year: 2022).*

Chen et al., Fabrication of humidity-sensitive polymer films, Dianzi Yuanjian Yu Cailiao, 21(12):24-6(2002), English abstract—Chinese publication.

De Boos, Non-crosslinking cationic polymers for the shrink-resistant treatment of wool, J. Textile Institute, 75(3):184-90 (1984).

Fefelova et al., Mucoadhesive interactions of amphiphilic cationic copolymers based on [2-(methacryloyloxy)ethyl]trimethylammonium chloride, Int J. Pharm., 339(1-2):25-32 (Jul. 2007).

Hardin et al., Hydrophobic Functionalization of Polyacrylic Acid as a Versatile Platform for the Development of Polymer Lipid Nanodisks, Small, 15(9):e1804813 (2019).

Kim et al., The design of polymer-based nanocarriers for effective transdermal delivery, Macromol. Biosci., 10(10):1171-6 (Oct. 2010).

Konar et al., Water-soluble quaternary amine polymers as controlled release carrier, J. Appl. Polymer Sci., 69(2):263-9 (1998).

Lee et al., A method for detergent-free isolation of membrane proteins in their local lipid environment, Nat. Protoc., 11(7):1149-62 (Jul. 2016).

Ozaki et al., Micellar electrokinetic chromatography using high-molecular-mass surfactants: comparison between anionic and cationic surfactants and effects of modifiers, J. Chromatography A, 709(1):3-10(1995).

Prade et al., A Minimal Functional Complex of Cytochrome P450 and FBD of Cytochrome P450 Reductase in Nanodiscs, Angew Chem. Int. Ed. Engl., 57(28):8458-62 (2018).

Ravula et al., pH Tunable and Divalent Metal Ion Tolerant Polymer Lipid Nanodiscs, Langmuir, 33:10655-62 (2017).

Svec et al., Design of a toolbox for fabrication of analytical microfluidic systems using porous polymer monoliths, pp. 643-645, Micro Total Analysis Systems 2001, Proceedings of the μTAS 2001 Symposium, held in Monterey, CA, USA Oct. 21-25, 2001.

Tada et al., Anti-biofouling properties of polymers with a carboxybetaine moiety, Macromol. Biosci., 9(1):63-70 (Jan. 2009).

Van Wagenen et al., Streaming potential investigations: polymer thin filsm, J. Colloid and Interface Science, 84(1):155-62 (1981).

Yasuhara et al., Spontaneous lipid nanodisc fomation by amphiphilic polymethacrylate copolymers, J. Am. Chem. Soc., 139:18657-63 (2017).

Zhang et al., Synthesis and characterization of resistive-type copolymer humidity sensitive materials, Gongneng Cailiao, 31 (Suppl):79-81 (2000), not in English.

Fiori et al., Polymer-encased nanodiscs with improved buffer compatibility, Sci. Rep., 7(1):7432 (Aug. 2017).

* cited by examiner

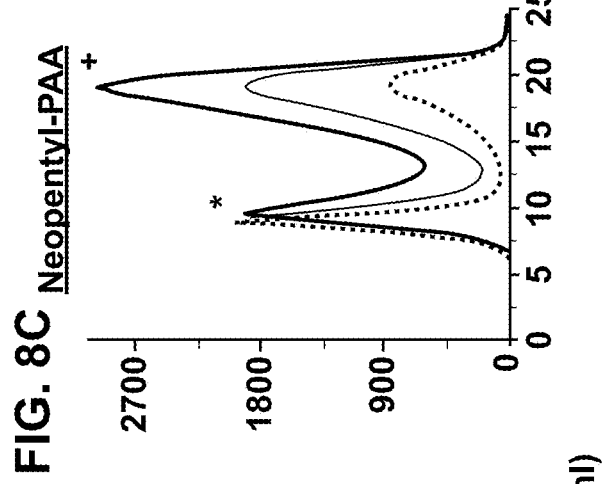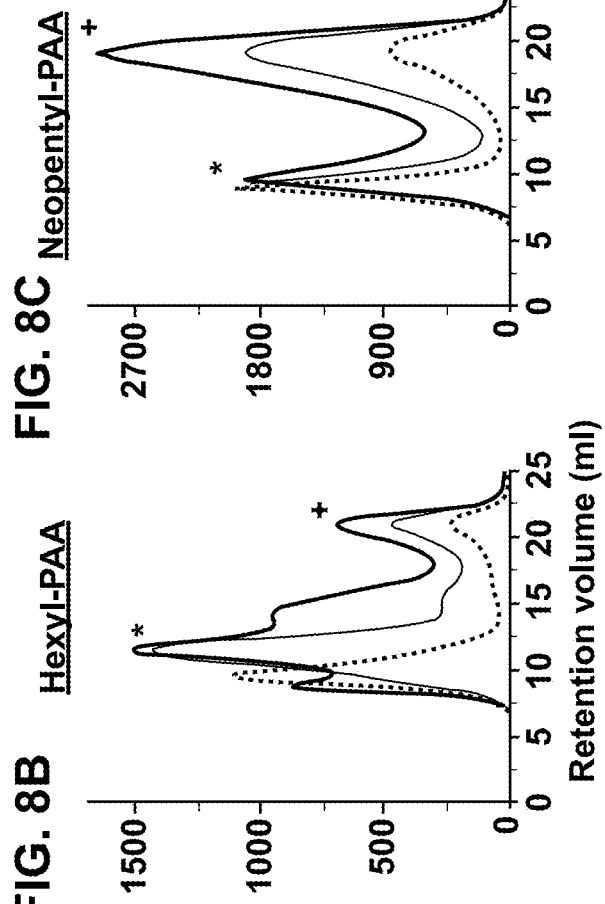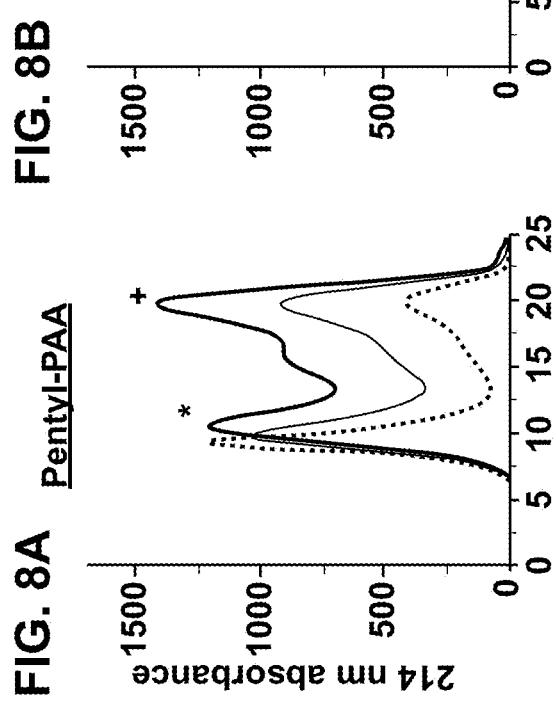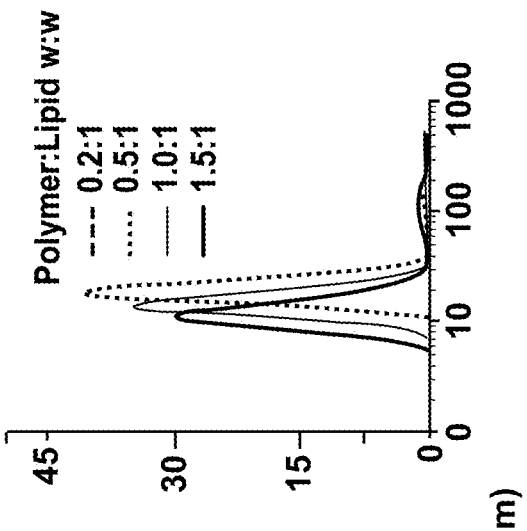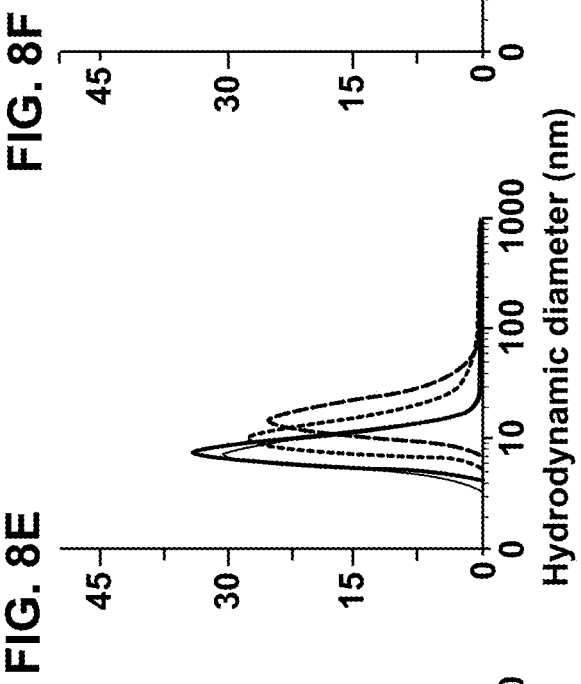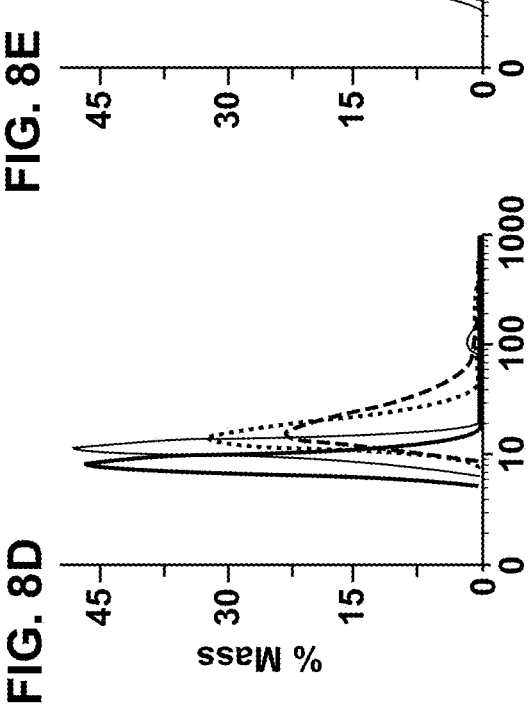

LIPID NANODISC FORMATION BY POLYMERS HAVING A PENDANT HYDROPHOBIC GROUP

CROSS-REFERENCE TO RELATED APPLICATIONS

Priority is claimed to U.S. Provisional Patent Application No. 62/858,724, filed Jun. 7, 2019, the entire disclosure of which is incorporated herein by reference.

STATEMENT OF GOVERNMENT SUPPORT

This invention was made with government support under GM084018 awarded by the National Institutes of Health. The government has certain rights in the invention.

FIELD OF THE DISCLOSURE

The disclosure relates generally to lipid nanodiscs. In particular, the disclosure relates to lipid nanodiscs formed from polymers comprising hydrophobic and hydrophilic groups.

BACKGROUND

Determination of the structure and function of membrane proteins is a challenge due to the difficulty of developing methods of extracting membrane proteins from their native environment, while preserving the correct conformation of the protein in isolation from its native environment. Traditional protocols involve extracting membrane proteins from their native environment using detergents and then including the proteins in a model bilayer system. Unfortunately, the use of detergents leads to issues such as protein inactivation and sample aggregation.

In order to avoid the use of detergents, methods for the isolation, purification, and characterization of membrane proteins have been developed which reconstitute membrane proteins in nanodiscs. Nanodiscs are disc-shaped patches of lipid bilayers surrounded by an amphiphilic belt. Amphiphilic belts that have been used in preparing nanodiscs include different sized membrane scaffold proteins, peptides, and polymers. Membrane scaffold protein-based nanodiscs are good mimics of the membrane; however, the reconstitution of the membrane proteins still require the use of detergents. Additionally, protein-based nanodiscs are restricted to a narrow range of size, difficult to prepare, and expensive to produce. Peptide-based nanodiscs are also limited by several disadvantages, including stability issues, interference from the peptides in biophysical measurements, and are expensive to produce. Similarly, copolymer-based nanodiscs are limited by disadvantages including restricted size range, their non-tolerance in the presence of divalent metal ions and different pH, and are expensive to produce. Thus, a need exists for nanodiscs that can address these difficulties.

SUMMARY

One aspect of the disclosure provides a lipid nanodisc comprising a lipid bilayer comprising a first hydrophilic face and a second hydrophilic face opposing the first hydrophilic face, and a hydrophobic edge between the opposing hydrophilic faces, and a polymer encircling the hydrophobic edge of the lipid bilayer, wherein the polymer comprises a first monomeric unit having a pendant hydrophobic group and a second monomeric unit having a backbone hydrophilic group.

Another aspect of the disclosure provides a method of making a lipid nanodisc, the method comprising contacting a lipid and a polymer comprising a first monomeric unit having a pendant hydrophobic group and a second monomeric unit having a backbone hydrophilic group to form a lipid nanodisc comprising a lipid bilayer comprising a first hydrophilic face and a second hydrophilic face opposing the first hydrophilic face, and a hydrophobic edge between the opposing hydrophilic faces, and the polymer encircling the hydrophobic edge of the lipid bilayer.

Another aspect of the disclosure provides a lipid nanodisc comprising a lipid bilayer comprising a first hydrophilic face and a second hydrophilic face opposing the first hydrophilic face, and a hydrophobic edge between the opposing hydrophilic faces, and a modified polyacrylic acid polymer encircling the hydrophobic edge of the lipid bilayer, wherein the modified polyacrylic acid comprises a backbone hydrophilic group and a pendant hydrophobic group.

Another aspect of the disclosure provides a method of making a lipid nanodisc, the method comprising modifying a polyacrylic acid polymer to include a pendant hydrophobic group, wherein said modifying comprises admixing a polyacrylic acid polymer with a compound comprising a hydrophobic group and a functional group capable of coupling with polyacrylic acid, thereby forming a modified polyacrylic acid comprising a hydrophilic group and a pendant hydrophobic group, and contacting a lipid with the modified polyacrylic acid polymer to form a lipid nanodisc, said lipid nanodisc comprising a lipid bilayer comprising a first hydrophilic face and a second hydrophilic face opposing the first hydrophilic face, and a hydrophobic edge between the opposing hydrophilic faces and the polymer encircling the hydrophobic edge of the lipid bilayer.

Another aspect of the disclosure provides a method of characterizing a membrane protein, the method including contacting a lipid nanodisc of the disclosure with a membrane protein to form a membrane protein-nanodisc including the membrane protein spanning across the lipid bilayer from the first hydrophilic face to the second hydrophilic face, and characterizing the lipid nanodisc including the membrane protein.

Further aspects and advantages will be apparent to those of ordinary skill in the art from a review of the following detailed descriptions. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 8A shows a sample size exclusion chromatogram of pentyl-PAA.

FIG. 8B shows a sample size exclusion chromatogram of hexyl-PAA.

FIG. 8C shows a sample size exclusion chromatogram of neopentyl-PAA.

FIG. 8D shows a sample dynamic light scattering profile of pentyl-PAA.

FIG. 8E shows a sample dynamic light scattering profile of hexyl-PAA.

FIG. 8F shows a sample dynamic light scattering profile of neopentyl-PAA.

DETAILED DESCRIPTION

Figure 1:
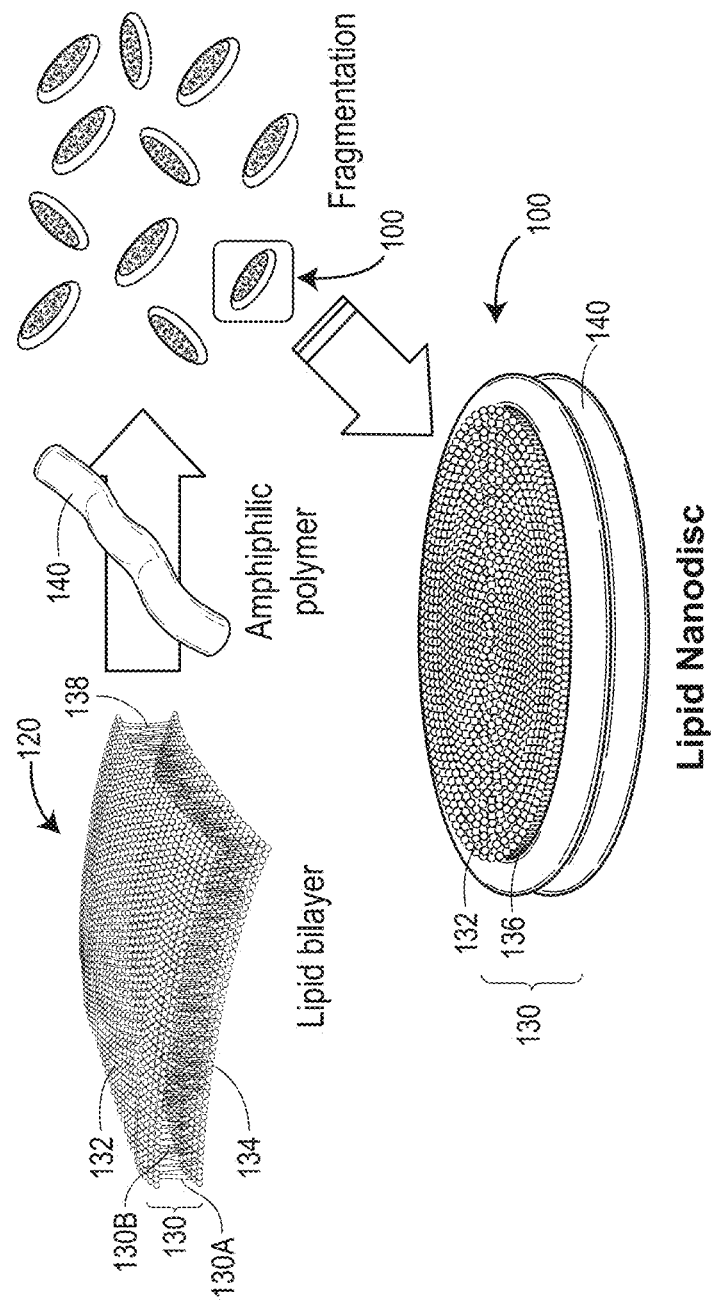
FIG. 1 shows a simplified schematic representation of lipid nanodisc formation.

Provided herein are polymer-based lipid nanodiscs and methods of making and using same. The polymer-based lipid nanodiscs disclosed herein can include an acryloyl-based copolymer comprising a monomeric unit having a pendant hydrophilic group and a monomeric unit having a pendant hydrophobic group. Alternatively, or additionally, the lipid nanodiscs disclosed herein can include a polymer including a first monomeric unit having a pendant hydrophobic group and a second monomeric unit having a backbone hydrophilic group. In embodiments, the polymer including a first monomeric unit having a pendant hydrophobic group and a second monomeric unit having a backbone hydrophilic group can be a modified polyacrylic acid, a modified polyacryloyl chloride, or a combination thereof.

The polymers and copolymers described herein provide one or more advantages, for example, extracting membrane proteins without the use of low-molecular weight detergents, forming nanodiscs with native lipid bilayers, solubilization of lipid bilayers, and forming nanodiscs over wide pH ranges and sizes. Additionally, the polymers and copolymers are advantageously stable for periods of at least 6 months, can be stored as powders, and do not require purification by high performance liquid chromatography. Furthermore, the lipid nanodiscs of the disclosure provide the unique advantage of enabling the application of various biophysical techniques typically employed in the structural study of membrane proteins, such as circular dichroism, UV/vis, and fluorescence spectroscopy, which may be otherwise unsuitable for lipid nanodiscs previously reported in the art.

Acryloyl-Based Copolymer

The copolymer of the disclosure can be an acryloyl-based copolymer comprising a first monomeric unit having a pendant hydrophobic group and a second monomeric unit having a pendant hydrophilic group. As used here, the term "acryloyl-based" means the copolymer of the disclosure is formed, in part or in whole, from monomers including or derived from an acryloyl group (e.g., a carbonyl group (C=O) bonded to a carbon α to an alkenyl group (C=C) such as a vinyl group). As used herein, the term "derived from" means that the monomeric unit is formed from the polymerization of the indicated monomer. For example, a monomeric unit derived from acrylic acid,

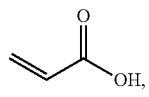

can have a structure of

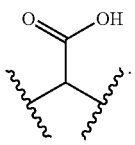 [SMILES: *C(*)C(=O)O]

Polymers can include multiple distinct monomeric units resulting from the polymerization of different monomers. For example, suitable monomers including or derived from an acryloyl group can be acrylic carbonyls, such as acrylic acid or acryloyl chloride. As used herein, and unless specified otherwise, "acryloyl-based" encompasses monomers including or derived from acrylate, alkacrylate (e.g., methacrylate), acrylamide, and/or alkacrylamide (e.g., methacrylamide). For example, at least 75 mol %, at least 80 mol %, at least 90 mol %, at least 95 mol %, at least 97 mol %, or at least 99 mol % of the monomeric units of an acryloyl-based copolymer are derived from acryloyl monomers as alkenyl or vinyl polymerization reaction products thereof.

As used herein, the term "backbone hydrophilic group" refers to a hydrophilic group wherein a carbon adjacent to or part of the hydrophilic group is directly attached to the polymer backbone. For example, when the hydrophilic group is a carboxylic acid, the backbone hydrophilic group has a structure of

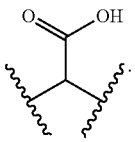

Such a backbone hydrophilic group is distinct from a pendant hydrophilic group, wherein a carbon adjacent to or part of the hydrophilic group is separated from the polymer backbone by two or more bonds. As used herein, "alkylene" refers to a bivalent saturated aliphatic radical. The term $C_n$ means the alkylene group has "n" carbon atoms. For example, $C_{1-6}$ alkylene refers to an alkylene group having a number of carbon atoms encompassing the entire range (i.e., 1 to 6 carbon atoms) as well as all subgroups (e.g., 1-5, 2-6, 3-6, 4-6, 0-4, 1-4, 2-4, 3-4, 0-3, 1-3, 2-3, 0-2, 1-2, 0, 1, 2, 3, 4, 5, and 6 carbon atoms). An alkylene can branched or linear. Optionally, the alkylene can be substituted, for example, with one or more of —$CO_2H$, —$NH_2$, —$NH_3+$, —OH, or —$SO_3H$ groups.

The copolymer of the disclosure can include a first monomeric unit having a pendant hydrophobic group and a second monomeric unit having a pendant hydrophilic group. Without intending to be bound by theory, it is believed that the hydrophobic pendant groups and hydrophilic pendant groups of the copolymer interact with the hydrophobic acyl chains and hydrophilic anionic phosphate headgroup of lipids, respectively, to enable the formation of a lipid nanodisc formation surrounded by the copolymer. A simplified schematic representation of the formation of lipid nanodiscs is shown in FIG. 1.

In some embodiments, the copolymer can be a random copolymer. The inventors have surprisingly and advantageously found that the copolymers of the disclosure, regardless of the arrangement of hydrophilic and hydrophobic monomers in the copolymer structure, mimic the structure of natural amphipathic α-helical peptides that have been found to form nanodiscs. By the use of hydrophilic and hydrophobic pendant groups, the inventors have found a copolymer that provides an amphipathic structure upon interaction with a lipid bilayer.

In embodiments, at least one of the first monomeric unit and the second monomeric unit is derived from an acrylate, an acrylamide, a $C_{1-6}$ alkylacrylate (e.g., $C_1$, $C_2$, or $C_3$ alkylacrylate), or a $C_{1-6}$ alkylacrylamide (e.g., $C_1$, $C_2$, or $C_3$ alkylacrylamide).

The copolymer of the disclosure can comprise a first monomeric unit and a second monomeric unit, wherein the first monomeric unit and the second monomeric unit are independently selected from the group consisting of a polymerization reaction product of an acrylate according to Formula 1 and a polymerization reaction product of an acrylamide according to Formula 2:

$$R_1R_2C=CR_3-C(=O)-O-R_4 \qquad (1)$$

$$R_1R_2C=CR_3-C(=O)-NR_4R_5 \qquad (2)$$

wherein $R_1$, $R_2$, $R_3$, and $R_5$ are independently selected from H and $C_{1-6}$ alkyl (e.g., $C_1$, $C_2$, or $C_3$ alkyl), and $R_4$ is the pendant hydrophobic group for the first monomeric unit or the pendant hydrophilic group for the second monomeric unit.

In addition to, or in the alternative of, the first monomeric unit and second monomeric unit being selected from the group consisting of a polymerization reaction product of an acrylate according to Formula 1 and a polymerization reaction product of an acrylamide according to Formula 2, the copolymer can comprise monomeric units that are not acryloyl-based. In embodiments wherein non-acryloyl-based monomeric units are included, the molecular weight is less readily controlled during the polymerization process. In some embodiments, the polymer can be derived from the polymerization of more than two monomer species. That is, the polymer can be derived from three (terpolymer), four (quaterpolymer), five, six, seven, or more different monomer species, whether acryloyl-based monomers, non-acryloyl-based monomers, or combinations thereof.

As used herein, "non-acryloyl-based" monomeric units include any monomeric unit that does not include or is not derived from an acryloyl group. Suitable non-acryloyl-based monomeric units are known in the art and can be derived from monomers including, but not limited to, vinyl alkanes (e.g., ethylene, propylene, butylene), vinyl acetates, vinyl ethers, vinyl alcohols (e.g., 1-hexen-6-ol) or combinations of the foregoing. Examples of non-acryloyl-based monomeric units include, but are not limited to, substituted or unsubstituted 1-hexen-6-ol, 1-hexene, propylene, α-butylene (1-butene), 1-pentene, 3-methyl-1-butene (isopentene), 4-methyl-1-pentene, 3-methyl-1-pentene, 2-methyl-1-pentene, 3,3-dimethyl-1-butene, and 2,3-dimethyl-1-butene.

The hydrophobic pendant group is not particularly limited. Suitable hydrophobic pendant groups include, but are not limited to, $C_{4-14}$ hydrocarbons (e.g., at least $C_4$, $C_6$, or $C_6$ hydrocarbons and/or up to $C_8$, $C_{10}$, $C_{12}$, or $C_{14}$ hydrocarbons). As used herein, the term "hydrocarbon" refers to any straight-chained, branched, or cyclic group including or consisting of carbon and hydrogen, wherein the group can be saturated or unsaturated. In some embodiments, the hydrocarbon can be a fluorinated hydrocarbon, wherein one or more of the hydrogen atoms of the hydrocarbon has been replaced with a fluorine atom. Examples of suitable fluorinated hydrocarbons, include but are not limited to, perfluorooctane, perfluorohexane, hexafluoroethane, and perfluoromethylcyclohexane. The term $C_n$ means the hydrocarbon has "n" carbon atoms. For example, $C_4$ hydrocarbon refers to a hydrocarbon that has four carbon atoms. $C_{1-7}$ refers to a hydrocarbon having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of hydrocarbon groups include methyl, ethyl, n-propyl, isopropyl, n-butyl, sec-butyl (2-methylpropyl), t-butyl (1,1-dimethylethyl), 3,3-dimethylpentyl, 2-ethylhexyl, n-octyl, n-nonyl, and n-decyl. Unless otherwise indicated, a hydrocarbon group can be an unsubstituted hydrocarbon group or a substituted hydrocarbon group.

The hydrophobic pendant group can comprise a linear $C_{4-14}$ hydrocarbon, a branched $C_{4-14}$ hydrocarbon, a cyclic $C_{4-14}$ hydrocarbon, or combinations thereof. In some embodiments, the linear $C_{4-14}$ hydrocarbon, the branched $C_{4-14}$ hydrocarbon, or the cyclic $C_{4-14}$ hydrocarbon is a fluorinated hydrocarbon. In some embodiments, the hydrocarbon is a saturated hydrocarbon. In other embodiments, the hydrocarbon is an unsaturated hydrocarbon. Without intending to be bound by theory, hydrophobic pendant groups having unsaturated hydrocarbons can result in decreased polymerization rates and, therefore, decreased copolymer yield, as the unsaturated groups can interfere with the free-radical polymerization reaction. However, copolymers comprising unsaturated hydrophobic pendant groups can still effectively form the lipid nanodiscs of the disclosure.

In some embodiments where the hydrocarbon is unsaturated, the unsaturation suitably is not conjugated. Without intending to be bound by theory, it is believed that conjugation in the pendant hydrophobic and/or hydrophilic group can cause interference in the absorption properties of the membrane proteins that can be associated with the lipid nanodiscs of the disclosure. Such interference can inhibit the use of commonly used biophysical techniques such as fluorescence, UV/vis and circular dichroism. Accordingly, in embodiments, the copolymers of the disclosure are free of styrene. In embodiments, the copolymers are free of all aromatic groups. As used herein, "free of all aromatic groups" means that the polymer contains less than 5 mol %, 3 mol %, 1 mol %, 0.5 mol %, 0.1 mol %, or 0.01 mol % of aromatic groups, based on the total amount of monomeric units in the polymer.

Examples of suitable $R_4$ groups for the first monomeric unit as seen in Formulas (1) and (2) include, but are not limited to —$CH_3$, —$CH_2CH_3$, —$CH_2CH_2CH_3$, —$CH_2CH_2CH_2CH_3$,

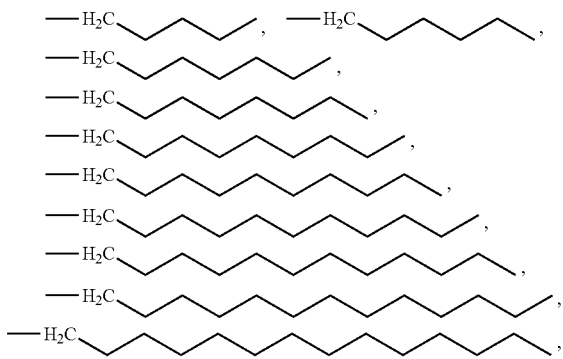

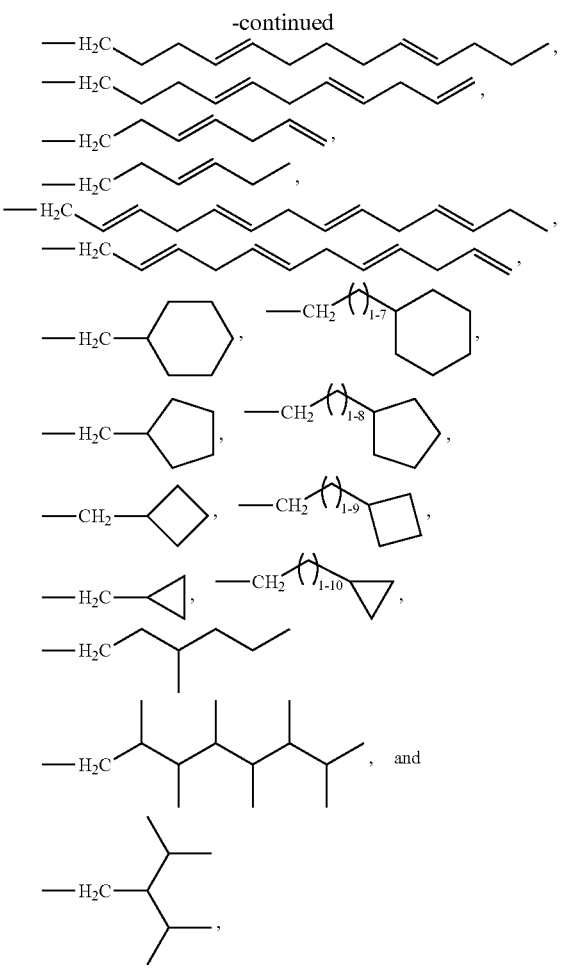

as well as partially or per-fluorinated analogs of the foregoing.

The second monomeric unit having a pendant hydrophilic group is not particularly limited, that is, it can include any hydrophilic group suitable to solubilize the lipid nanodisc in an aqueous solution. In some embodiments, the pendant hydrophilic group can include one or more of hydroxyl, amino, ether, carboxylic acid, carboxylate, phosphate, phosphonate, phosphocholine, carboxylic ether, carboxylic ester, phosphate ester, amide, phosphonamide, ammonium, or salts of the foregoing. The pendant hydrophilic group can be positively charged, negatively charged, zwitterionic, or neutral. Positively charged hydrophilic groups can include, but are not limited to, ammonium cations (e.g. alkylammonium cations, such as mono-, di-, tri-, or tetra-alkylammonium cations). Negatively charged hydrophilic groups can include, but are not limited to, carboxylate or phosphate.

The pendant hydrophilic group can be a chelating group or can further include a chelating group. The chelating group can further include a metal ion bound thereto. A pendant hydrophilic group including a fluorescent group or chelating group having a metal ion bound thereto can advantageously provide a spectroscopic tag to provide additional characterization of the lipid nanodiscs including the copolymers of the disclosure. Suitable fluorescent tags can include, but are not limited to, cyanine5 amine and Alexa fluor 488. Suitable metal chelating tags include, but are not limited to, ethylenediaminetetraacetic acid (EDTA) and lanthanide binding tags.

Examples of suitable $R_4$ groups for the second monomeric unit, as seen in Formulas (1) and (2) include, but are not limited to:

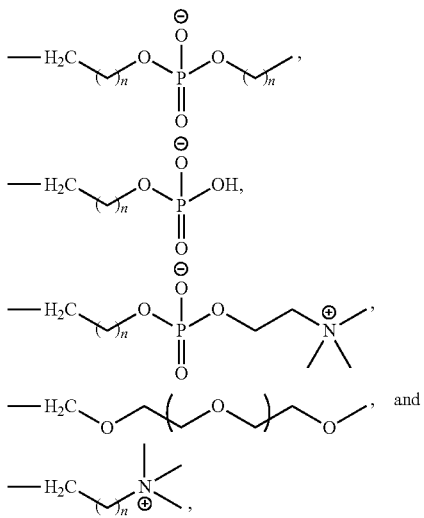

wherein n can be between 1 and 14, such as

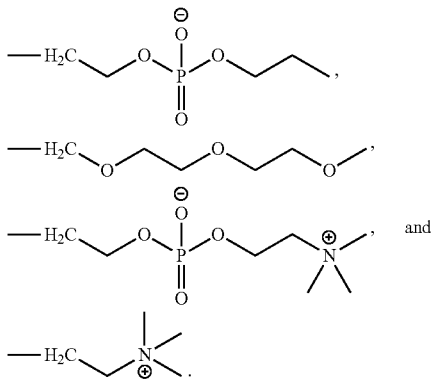

In some embodiments, the first monomeric unit is derived from butyl methacrylate. In some embodiments, the second monomeric unit is derived from a methacroylcholine salt. More specifically, the second monomeric unit can be derived from methacroylcholine chloride. In some embodiments, the copolymer comprises a first monomeric unit derived from butyl methacrylate and a second monomeric unit derived from methacroylcholine chloride.

The acryloyl-based copolymer of the disclosure can comprise monomeric units having a pendant hydrophobic group at a mole fraction of about 0.20 to about 0.90, based on the total number of monomeric units having a pendant hydrophobic group and monomeric units having a pendant hydrophilic group. As used herein, this mole fraction, f, can also be referred to as the "hydrophobicity" or "hydrophobic fraction." In embodiments, the hydrophobic fraction ranges from about 0.20 to about 0.90, about 0.24 to about 0.85, or about 0.40 to about 0.60, for example about 0.20, 0.24, 0.25, 0.26, 0.33, 0.39, 0.40, 0.43, 0.44, 0.50, 0.51, 0.55, 0.59, 0.60, 0.61, 0.62, 0.63, 0.65, 0.70, 0.71, 0.75, 0.80, 0.85, or 0.90. Without intending to be bound by theory, it is believed that as the hydrophobicity decreases, e.g., below about 0.2, the interaction of the copolymer, as a whole, with the hydrophobic regions of the lipid bilayer decreases, thereby decreasing or inhibiting the ability of the copolymer to solubilize the lipid bilayer and/or induce fragmentation of a lipid bilayer to form nanodiscs. Similarly, without intending to be bound by theory, as the hydrophobicity increases, e.g., above about 0.8, the interaction of the copolymer, as a whole, with the hydrophobic regions of the lipid bilayer increases, resulting in the formation of small particles likely to be spherical polymer micelles, rather than the desired lipid nanodiscs.

The molecular weight of the acryloyl-based copolymer of the disclosure is not particularly limited. The copolymer can have a number-average molecular weight ($M_n$) in a range from about 1.5 kg/mol to about 15 kg/mol, about 1.7 kg/mol to about 14 kg/mol, or about 3.0 kg/mol to about 9.0 kg/mol, for example, about 1.5, 1.7, 2.0, 2.9, 3.7, 3.9, 4.0, 4.2, 4.3, 4.7, 5.5, 6.1, 6.3, 6.7, 6.9, 7.1, 7.3, 7.4, 8.7, 9.0, 10.0, 11.0, 12.0, 13.0, 14.0, or 15.0 kg/mol. Without intending to be bound by theory, it is believed that as the number-average molecular weight of the copolymer decreases, the ability of the copolymer to disrupt a lipid vesicle and form a lipid nanodisc decreases because the size (width) of the polymer band that forms around the lipid nanodisc decreases. Further, it is believed that when the number-average molecular weight decreases beyond, e.g., 3 kg/mol or 1.5 kg/mol, the size of the resulting polymer band becomes too narrow to span the hydrophobic edge of the lipid bilayer, thereby inhibiting or preventing nanodisc formation. Accordingly, the number-average molecular weight of the polymer can be selected to promote nanodisc formation and stability. In general, a low molecular weight polymer in the foregoing ranges permits improved control over the size of the formed nanodiscs. If the molecular weight of the copolymer decreases beyond 1.0 kg/mol, however, the copolymer can behave as a detergent, leading to issues such as protein inactivation and sample aggregation. In addition, without intending to be bound by theory, it is believed that as the number-average molecular weight of the copolymer increases, the interaction of the copolymer with the lipid bilayer, as well as the inter- and intra-polymer interactions, increase, thereby providing a heterogeneous mixture of small particles and large fragments of lipid vesicles, rather than the desired lipid nanodiscs. Furthermore, if the molecular weight of the copolymer increase above, for example 15 kg/mol, the efficiency of nanodisc formation can decrease as a result of the increased viscosity of the copolymer solution.

The degree of polymerization (DP) of the copolymer is not particularly limited. The degree of polymerization of the acryloyl-based copolymer can range from about 10 to about 100, about 15 to about 95, about 30 to about 70, or about 40 to about 60, for example about 10, 12, 18, 20, 23, 24, 27, 28, 30, 35, 36, 37, 40, 41, 43, 48, 50, 55, 56, 60, 65, 70, 75, 78, 80, 82, 83, 90, 95 or 100.

Polymer Including a First Monomeric Unit Having a Pendant Hydrophobic Group and a Second Monomeric Unit Having a Backbone Hydrophilic Group The polymer used to prepare the lipid nanodiscs of the disclosure can include a first monomeric unit having a pendant hydrophobic group and a second monomeric unit having a backbone hydrophilic group. It is well understood in the art that a polymer is made up of a plurality of monomers bonded together. Once polymerized, the monomers can be considered to have been converted to monomeric units, which make up the polymer backbone and may or may not be further modified. For example, the polymer can, optionally, be further modified to include a pendant hydrophilic group.

The polymer can generally prepared by admixing a polyacrylic acid or a polyacryloyl chloride with a compound including a hydrophobic group and a functional group capable of coupling with a polyacrylic acid or a polyacryloyl chloride, to provide, for example, a modified polyacrylic acid polymer or a modified polyacryloyl chloride polymer.

As used here, the term "modified polyacrylic acid polymer" means the polyacrylic acid polymer of the disclosure has been formed by the polymerization of acrylic acid monomers, and subsequently modified to include a pendant hydrophobic group. Similarly, the modified polyacrylic acid polymer can, optionally, be further modified to include a pendant hydrophilic group. Modification of a polyacrylic acid polymer can occur, for example, through a condensation reaction or a nucleophilic substitution reaction (e.g. Fischer esterification). In embodiments, the compound including the hydrophobic group and a functional group capable of coupling with a polyacrylic acid includes, for example, $C_{1-9}$ alkyl amine, benzyl amine, aniline, pyrene, aminoadamantane, or $C_{1-8}$ alcohol. In embodiments, the compound including the hydrophobic group and a functional group capable of coupling with a polyacrylic acid includes a hydrophobic group as provided for Formulas (1) and (2), above. Examples of suitable $C_{1-9}$ alkyl amines include n-butyl amine, tert-butyl amine, sec-butyl amine, pentyl amine, hexyl amine, and neopentyl amine. In embodiments, the compound including a hydrophobic group and a functional group capable of coupling with a polyacrylic acid includes n-butyl amine, pentyl amine, hexyl amine, neopentyl amine, or any combination thereof.

The polymer can also be prepared by nucleophilic addition of an amine or an alcohol to an acid chloride, by admixing a polyacryloyl chloride with a compound including a hydrophobic group and an amine or an alcohol. The polyacryloyl chloride can be prepared by converting polyacrylic acid to polyacryloyl chloride, or from direct synthesis of the polyacryloyl chloride from acryloyl chloride (acrylic acid chloride). Methods of converting carboxylic acids to acid chlorides are well known in the art.

The polymer having a first monomeric unit comprising a pendant hydrophobic group and a second monomeric unit having a backbone hydrophilic group of the disclosure can include, as the first monomeric unit, a monomeric unit having a structure according to Formula 3 or Formula 4:

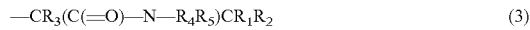
$$—CR_3(C(=O)—N—R_4R_5)CR_1R_2— \quad (3)$$

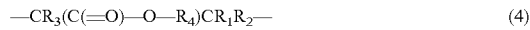
$$—CR_3(C(=O)—O—R_4)CR_1R_2— \quad (4)$$

wherein each of $R_1$, $R_2$, $R_3$, and $R_5$ is independently selected from H and $C_{1-6}$ alkyl (e.g., $C_1$, $C_2$, $C_3$, $C_4$, $C_6$ or $C_6$ alkyl), and $R_4$ is the pendant hydrophobic group. In embodiments, $R_4$, or the pendant hydrophobic group, can be any hydrophobic group suitable for use in a lipid nanodisc, as provided for Formulas (1) and (2), above. Furthermore, in some embodiments, $R_4$ can include unsaturated, conjugated, and/or aromatic groups. In embodiments, $R_4$ includes $C_{0-3}$ alkylene-phenyl, pyrene, adamantane, or a combination thereof. For example, in embodiments, $R_4$ includes phenyl, benzyl, adamantane, pyrene, or a combination thereof.

The polymer further comprises a monomeric unit having a backbone hydrophilic group. In some embodiments, the backbone hydrophilic group is provided by unmodified polyacrylic acid monomeric units in the backbone of the polymer. Backbone hydrophilic groups can also be provided by converting acryloyl chloride units of polyacryloyl chloride to carboxylic acid groups, which is known to readily occur in the presence of water. Advantageously, and without intending to be bound by theory, it is believed that these backbone hydrophilic groups (e.g., unmodified polyacrylic acid monomeric units) can interact with the aqueous medium to assist in solubilization of the center portion of the lipid nanodisc, which is otherwise hydrophobic, thereby assisting in the solubilization of the lipid nanodisc, as a whole. Furthermore and surprisingly, although the hydrophilic groups of the polymer do not directly interact with the hydrophilic head groups of the lipids in the lipid nanodisc, the polymers of the disclosure can still effectively enable formation of a lipid nanodisc and solubilize the lipid nanodiscs.

In embodiments, the backbone hydrophilic group can be modified to include a pendant hydrophilic group, thereby providing a polymer having a first monomeric unit having a pendant hydrophobic group and a second monomeric unit having a pendant hydrophilic group. The polymer having a pendant hydrophilic group can be prepared in a manner similar to that used to provide the pendant hydrophobic group (e.g., a condensation reaction or nucleophilic substitution reaction between a carboxyl group and a compound including an amine or an alcohol, or nucleophilic addition of a compound including an amine or an alcohol to a polyacryloyl chloride), to include the pendant hydrophilic group on the second monomeric unit. Examples of suitable pendant hydrophilic groups are provided above, with respect to Formulas (1) and (2). In some embodiments, the pendant hydrophilic group includes one or more of hydroxyl, amino, ether, carboxylic acid, carboxylate, phosphate, phosphonate, phosphocholine, carboxylic ether, carboxylic ester, phosphate ester, amide, phosphonamide, ammonium, or salts of the foregoing.

The polymer having a first monomeric unit comprising a pendant hydrophobic group and a second monomeric unit having a backbone hydrophilic group of the disclosure can include, as the second monomeric unit, a monomeric unit having a structure according to Formula 5:

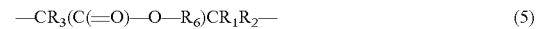
$$—CR_3(C(=O)—O—R_6)CR_1R_2— \quad (5)$$

wherein each of $R_1$, $R_2$, and $R_3$ is independently selected from H and $C_{1-6}$ alkyl (e.g., $C_1$, $C_2$, or $C_3$ alkyl), and $R_6$ is H.

In embodiments wherein the backbone hydrophilic group has been modified to provide a pendant hydrophilic group, the second monomeric unit can include a monomeric unit having a structure according to Formula (5):

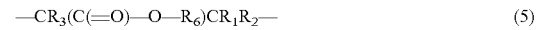
$$—CR_3(C(=O)—O—R_6)CR_1R_2— \quad (5)$$

wherein each of $R_1$, $R_2$, and $R_3$ is independently selected from H and $C_{1-6}$ alkyl (e.g., $C_1$, $C_2$, or $C_3$ alkyl), and $R_6$ is selected from $C_{1-6}$ alkylene-$R_7$, wherein $R_7$ comprises hydroxyl, amino, ether, carboxylic acid, phosphate, phosphonate, phosphocholine, carboxylic ether, carboxylic ester, phosphate ester, amide, phosphonamide, ammonium, sugar, amino sugar, —$(OR_8)_y$—H, or salts of the foregoing. In embodiments, $R_8$ can be $C_{1-4}$ alkylene and y can be 1, 2, 3, 4, 5, 6, 7, or 8. In some embodiments, $R_6$ is $C_{1-6}$ alkylammonium, $C_{1-6}$ alkylene-OH, or $C_{1-6}$ alkylene-$CO_2H$. In some embodiments, $R_8$ is ethylene. In embodiments, the alkylene of $R_6$ is substituted with one of more of —$CO_2H$, —$NH_2$, —$NH_3+$, —OH, or —$SO_3H$ groups. For example, in embodiments, $R_6$ can be $C_{1-6}$ alkylene-$R_7$ wherein $R_7$ is hydroxyl and the alkylene includes one or more substituted hydroxyl (i.e., —OH) groups. That is, in some cases, $R_6$ can include a polyol.

The hydrophilic group can be positively charged, negatively charged, zwitterionic, or neutral. Positively charged hydrophilic groups can include, but are not limited to, ammonium cations (e.g. alkylammonium cations, such as mono-, di-, tri-, or tetra-alkylammonium cations). Negatively charged hydrophilic groups can include, but are not limited to, carboxylate or phosphate. Neutrally charged hydrophilic groups can include hydroxyl and carboxylic acids.

In embodiments, the polymer is a random copolymer. For example, in some embodiments, the polymer can be derived from the polymerization of two or more monomer species. That is, the polymer can be derived from two, three (terpolymer), four (quaterpolymer), five, six, seven, or more different monomer species. In embodiments, the polymer is a random copolymer derived from acrylic acid and acryloyl chloride. For example, the monomeric units derived from acrylic acid can provide the backbone hydrophilic groups, while the monomeric units derived from acryloyl chloride can be modified to provide the pendant hydrophobic groups.

In embodiments, the polymer can include at least one monomeric unit selected from each of Formula 3, Formula 4, and/or Formula 5. The $R_1$, $R_2$, and $R_3$ groups of each of Formulas 3-5 can be the same or different between each of Formulas 3-5. For example, in embodiments wherein a polyacrylic acid polymer (or any other homopolymer) is modified to include pendant hydrophobic groups, as provided above, then each of $R_1$, $R_2$, and $R_3$ are the same for the first monomeric unit having a pendant hydrophobic group and the second monomeric unit having a backbone hydrophilic group. In embodiments wherein the polymer is a random copolymer (e.g. a poly(methacrylic acid-co-acrylic acid)), then each of $R_1$, $R_2$ and $R_3$ can be different for the first monomeric unit having a pendant hydrophobic group and the second monomeric unit having a backbone hydrophilic group.

In embodiments, the polymer comprises a randomized distribution of the pendant hydrophobic group(s) and/or backbone hydrophilic groups. In embodiments, the polymer comprises an alternating distribution of pendant hydrophobic monomeric units and backbone hydrophilic groups or a non-random non-alternating distribution of pendant hydrophobic monomeric units and backbone hydrophilic groups (e.g., a repeating —(O—W)— structure wherein O represents 2, 3, 4, or more pendant hydrophobic monomeric units and W represents 2, 3, 4, or more backbone hydrophilic groups and the number of pendant hydrophobic monomeric units and number of backbone hydrophilic groups represented by O and W can be the same or different). In embodiments, the polymer comprises a block distribution of the pendant hydrophobic monomeric units and the backbone hydrophilic groups.

Without intending to be bound by theory, it is believed that conjugation in the backbone or pendant hydrophilic group and/or pendant hydrophobic group can cause interference in the absorption properties of the membrane proteins that can be associated with the lipid nanodiscs of the disclosure. Such interference can inhibit the use of commonly used biophysical techniques such as fluorescence, UV/vis and circular dichroism. Accordingly, in embodiments, the polymers of the disclosure are free of styrene. In embodiments, the polymers are free of aromatic groups.

The amount of first monomeric units in the polymer having a first monomeric unit comprising a pendant hydrophobic group and a second monomeric unit having a backbone hydrophilic group can be in a range of about 20 to about 90 mol %, about 24 to about 85 mol % or about 40 to about 60 mol %, for example about 20, 24, 25, 30, 35, 40, 45, 50, 55, 60, 65, 70, 75, 80, 85, or 90 mol %, based on the total amount of first and second monomeric units. That is, in embodiments, about 20 to about 90 mol % of the monomeric units of the polymer have pendant hydrophobic groups. In embodiments, about 24 to about 85 mol % of the monomeric units of the polymer have pendant hydrophobic groups. In embodiments, about 40 to about 60 mol % of the monomeric units of the polymer have pendant hydrophobic groups. The amount of first and second monomeric units can also be expressed as mole fractions based on the total amount of first and second monomeric units. Thus, the first monomeric unit can be present in the polymer at a mole fraction of about 0.2 to about 0.90, based on the total amount of the first and second monomeric units, about 0.24 to about 0.85 or about 0.40 to about 0.60, for example about 0.20, 0.24, 0.25, 0.30, 0.35, 0.40, 0.45, 0.50, 0.55, 0.60, 0.65, 0.70, 0.75, 0.80, 0.85, or 0.90, based on the total amount of first and second monomeric units.

The molecular weight of the polymer having a first monomeric unit comprising a pendant hydrophobic group and a second monomeric unit having a backbone hydrophilic group of the disclosure is not particularly limited. The polymer can have a number-average molecular weight ($M_n$) in a range from about 2.5 kg/mol to about 10 kg/mol, about 3.0 kg/mol to about 9.0 kg/mol, or about 4.0 kg/mol to about 7.0 kg/mol, for example, about 2.5, 3.0, 3.5, 4.0, 4.5, 5.0, 5.5, 6.0, 6.5, 7.0, 7.5, 8.0, 8.5, 9.0, 9.5, or 10 kg/mol. Without intending to be bound by theory, it is believed that as the number-average molecular weight of the polymer decreases, the ability of the polymer to disrupt a lipid vesicle and form a lipid nanodisc decreases because the size (width) of the polymer band that forms around the lipid nanodisc decreases. Further, it is believed that when the number-average molecular weight decreases beyond, e.g., 2.5 kg/mol, the size of the resulting polymer band becomes too narrow to span the hydrophobic edge of the lipid bilayer, thereby inhibiting or preventing nanodisc formation. Accordingly, the number-average molecular weight of the polymer can be selected to promote nanodisc formation and stability. In general, a low molecular weight polymer in the foregoing ranges permits improved control over the size of the formed nanodiscs. If the molecular weight of the polymer decreases beyond 1.0 kg/mol, however, the polymer can behave as a detergent, leading to issues such as protein inactivation and sample aggregation. In addition, without intending to be bound by theory, it is believed that as the number-average molecular weight of the polymer increases, the interaction of the polymer with the lipid bilayer, as well as the inter- and intra-polymer interactions, increase, thereby providing a heterogeneous mixture of small particles and large fragments of lipid vesicles, rather than the desired lipid nanodiscs. Furthermore, if the molecular weight of the polymer increase above, for example 15 kg/mol, the efficiency of nanodisc formation can decrease as a result of the increased viscosity of the polymer solution.

The degree of polymerization (DP) of the polymer having a first monomeric unit comprising a pendant hydrophobic group and a second monomeric unit having a backbone hydrophilic group is not particularly limited. The degree of polymerization of the polymer can range from about 10 to about 100, about 15 to about 95, about 30 to about 70, or about 40 to about 60, for example about 10, 12, 18, 20, 23, 24, 27, 28, 30, 35, 36, 37, 40, 41, 43, 48, 50, 55, 56, 60, 65, 70, 75, 78, 80, 82, 83, 90, 95 or 100.

Lipid Nanodiscs

The lipid nanodiscs of the disclosure generally include a lipid bilayer having a first hydrophilic face and a second hydrophilic face opposint the first hydrophilic face, and a hydrophobic edge between the opposing hydrophilic faces, and a polymer of the disclosure encircling the hydrophobic edge of the lipid bilayer. The lipid is not particularly limited. The lipid can include a natural cell membrane extract. Suitable lipids include, but are not limited to phosphatidylethanolamines, phosphatidylcholines, phosphatidylglycerols, phosphatidylserines, cholesterols, sphingomyelin, gangliosides, lipopolysaccharides, phophatidylinositols, and derivatives of the foregoing. In some embodiments, the lipid comprises at least one of phosphatidylethanolamines, phosphatidylcholines, phosphatidylglycerols, phosphatidylserines, cholesterols, sphingomyelin, gangliosides, lipopolysaccharides, and phophatidylinositols. In some embodiments, the lipid is a phospholipid. In some embodiments, the phospholipid includes a phosphatidylcholine.

FIG. 1 illustrates a lipid nanodisc 100 according to the disclosure, which includes a lipid 120 and a polymer or copolymer (e.g., an acryloyl-based copolymer, a modified polyacrylic acid polymer, or polymer having a first monomeric unit comprising a pendant hydrophobic group and a second monomeric unit having a backbone hydrophilic group) 140. The lipid 120 in the nanodisc 100 forms a lipid bilayer 130 including a first hydrophilic face 132 and a second hydrophilic face 134, wherein the first hydrophilic face 132 and the second hydrophilic face 134 are opposing, and a hydrophobic edge 136 between the opposing hydrophilic faces 132, 134. The hydrophobic edge 136 is made up of the hydrophobic tails 138 from both layers of the lipid bilayer 130. The center of the hydrophobic edge 136 is the point at which the hydrophobic tail 138 from one layer 130A of the bilayer 130 meets the hydrophobic tail 138 from the second layer 130B of the bilayer 130. The nanodisc 100 further includes a polymer or copolymer 140 of the disclosure encircling the hydrophobic edge 136 of the lipid bilayer 130.

The lipid nanodiscs of the disclosure can have a diameter in a range of about 6 nm to about 100 nm, for example, about 6 nm to about 100 nm, about 10 nm to about 90 nm, about 20 nm to about 90 nm, about 30 nm to about 80 nm, about 40 nm to about 80 nm, about 50 nm to about 70 nm, or about 55 nm to about 65 nm. In some embodiments, the nanodisc has a diameter less than or equal to 40 nm, for example, in a range of about 6 nm to 40 nm, about 10 nm to about 35 nm, about 6 nm to about 20 nm, about 20 nm to about 35 nm, or about 25 nm to about 30 nm. In some embodiments, the nanodisc has a diameter greater than 40 nm, for example, 41 nm to about 100 nm, about 45 nm to about 90 nm, about 50 nm to about 80 nm, about 50 nm to about 70 nm, or about 60 nm. Nanodiscs having a diameter greater than 40 nm can be referred to as "macrodiscs." The size of the nanodisc can be controlled by changing the lipid:polymer/polymer weight ratio during preparation. In general, as the amount of polymer or copolymer increases relative to the amount of lipid, the size of the resulting nanodisc decreases. Similarly, as the amount of polymer or copolymer decreases relative to the amount of lipid, the size of the resulting nanodisc increases.

In some embodiments, the lipid nanodisc can be characterized in that when a magnetic field is applied, the nanodisc aligns with the magnetic field. Such a characteristic can be advantageous, for example, when characterizing the nanodisc (or a membrane protein provided therein) by NMR spectroscopy.

The lipid nanodisc can further include a membrane protein. The membrane protein can be any protein that interacts with or is part of a biological membrane, and can be permanently anchored or temporarily anchored to a lipid bilayer. Suitable membrane proteins include, but are not limited to U-$^{15}$N Cytb5, cytochromes such as cytochrome b5, cytochrome P450, cytochrome P450 reductase, cytochrome c, outer membrane proteins or integral outer membrane proteins, photosystem II, voltage-gated ion channels, beta barrel, and G-protein-coupled receptors (GPCRs). When a membrane protein is included in the lipid nanodisc, the membrane protein spans across at least one half of the lipid bilayer, from one hydrophilic face to the center of the hydrophobic edge. In some embodiments, the membrane protein spans across the entire lipid bilayer from the first hydrophilic face to the second hydrophilic face at least once. In some embodiments, the membrane protein spans across the entire lipid bilayer from the first hydrophilic face to the second hydrophilic face more than once.

In embodiments, the lipid nanodisc further includes a drug. The drug can be incorporated in, encapsulated by, or entangled with the lipid nanodisc. When a drug is present in the lipid nanodisc, the lipid nanodisc can act as a drug-carrier and/or drug-delivery system. In general, the lipid nanodisc can be used as a drug carrier for any hydrophobic and/or low solubility drug. Suitable drugs include, but are not limited to, those classified as Class II and IV according to the Biopharmaceutical Classification System (BCS). BCS Class II drugs have high permeability and low solubility, and BCS Class IV drugs have low permeability and low solubility. These drugs generally must be administered in a formulation to increase their solubility and bioavailability. Examples of suitable drugs include, but are not limited to, benzylpenicillin, bicalutamide, bifonazole, glibenclamide, ezetimibe, and aceclofenac.

Method of Preparing Lipid Nanodisc

Further provided herein are methods of making a lipid nanodisc 100. In embodiments, the method includes contacting a lipid 120 and an acryloyl-based or other copolymer 140 comprising a copolymer formed by the polymerization of a monomer having a pendant backbone hydrophilic group and a monomer having a pendant hydrophobic group (FIG. 1). The method of making a lipid nanodisc can also include contacting a lipid and an acryloyl-based copolymer comprising a first monomeric unit having a pendant hydrophobic group and a second monomeric unit having a pendant hydrophilic group.

In embodiments, the method includes contacting a lipid with a polymer having a first monomeric unit comprising a pendant hydrophobic group and a second monomeric unit having a backbone hydrophilic group to form a lipid nanodisc.

In embodiments, the method includes modifying a polyacrylic acid polymer to include a pendant hydrophobic group, and contacting a lipid with the modified polyacrylic acid polymer to form a lipid nanodisc.

The modifying step can occur in the presence of a coupling agent. For example, in embodiments, the modifying step occurs in the presence of N-(3-dimethylaminopropyl)-N-ethylcarbodiimide hydrochloride (EDC), ethyl chloroformate, methyl chloroformate, benzyl chloroformate, hexafluorophosphate benzotriazole tetramethyl uronium (HBTU), hexafluorophosphate azabenzotriazole tetramethyl uronium (HATU), benzotriazol-1-yl-oxytripyrrolidinophosphonium hexafluorophosphate (PyBOP), (7-azabenzotriazol-1-yloxy)tripyrrolindinophosphonium hexafluorophosphate (PyAOP), N,N'-dicyclohexylcarbodiimide (DCC), or any combination thereof. In embodiments, the modifying occurs in an organic solvent, for example acetone, THF, DMF, or acetonitrile. In embodiments, the organic solvent comprises THF. The polyacrylic acid polymer used in the modifying step (i.e., the unmodified, starting polyacrylic acid polymer) can have a weight-average molecular weight ($M_w$) of about 1000 g/mol to about 6000 g/mol, for example, about 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, or 6000 g/mol.

Advantageously, the nanodiscs of the disclosure are easy to prepare, inexpensive and stable for up to a month. Furthermore, the nanodiscs of the disclosure can advantageously be characterized by common biophysical techniques, such as circular dichroism (CD), UV/Vis and fluorescence spectroscopy.

The lipid and polymer or copolymer can be any lipid and polymer or copolymer described herein. The method of preparing the lipid nanodisc includes contacting the lipid and the polymer or copolymer. In some embodiments, the lipid is provided as a multilamellar vesicle. Without intending to be bound by theory, it is believed that when the lipid is provided as a multilamellar vesicle, the polymer or copolymer chains get inserted into the lipid bilayer and break the multilamellar vesicle into nanodisc shaped lipoparticles. The lipid can include a natural cell membrane extract.

The lipid can further include a membrane protein such that the resulting lipid nanodisc includes a membrane protein spanning across at least one half of the lipid bilayer from one hydrophilic face to the center of the hydrophobic edge. In some embodiments, the lipid includes a membrane protein such that the resulting lipid nanodisc includes a membrane protein spanning across the entire lipid bilayer from one hydrophilic face to the second hydrophilic face at least once. In some embodiments, the membrane protein spans across the entire lipid bilayer from the first hydrophilic face to the second hydrophilic face more than once.

The contacting step can include admixing the lipid and the polymer or copolymer in solution. An aqueous solution of polymer or copolymer can be prepared prior to contacting the polymer or copolymer with the lipid. A lipid dispersion can be prepared prior to contacting the polymer or copolymer with the lipid. The contacting step can include admixing the polymer or copolymer solution and the lipid dispersion. The solutions, suspensions, and dispersions of the disclosure can be substantially free of a detergent. As used herein, "substantially free" means that the solution and/or suspension does not contain significant amounts of a purposefully added detergent. Thus, incidental or background quantity of detergents (e.g., less than about 100 ppb) can be present in the solution and/or suspension and be within the scope of the disclosure.

The contacting step can optionally further include providing a buffer to regulate the pH of the solution. Without intending to be bound by theory it is believed that in some embodiments, the pH of the solution can affect the charge of the polymer or copolymer, thus ultimately affecting solubility of the polymer or copolymer and stability of the resulting nanodiscs. The contacting step can be carried out at any suitable pH in which the polymer or copolymer is stable and soluble, for example, in a range of about 0 to about 14, about 1 to about 12, about 2 to about 11, about 2 to about 10, about 2.5 to about 10, about 3 to about 8, about 7 to about 12, or about 3 to about 9, for example, about 2.5, about 3, about 3.5, about 4, about 4.5, about 5, about 5.5, about 6, about 6.5, about 7, about 7.5, about 8, about 8.5, about 9, about 9.5, or about 10.

The weight ratio of the lipid to the polymer or copolymer of the disclosure provided in the methods of the disclosure is not particularly limiting. The lipid and the polymer or copolymer can be provided in a ratio of about 9:1 to about 1:9 by weight, for example, a weight ratio of about 8:1 to about 1:8, about 6:1 to about 1:6, about 4:1 to about 1:4, or about 1:1. In some embodiments, the lipid and the polymer or copolymer are provided in a ratio in a range of about 8:1 to about 1:3, by weight. In some embodiments, the lipid and the polymer or copolymer are provided in a ratio in a range of about 4:1 to about 1:1.5, or about 3:1 to about 1:1, by weight. In general, as the weight of the polymer or copolymer is increased relative to the weight of the lipid, the maximum diameter of the resulting nanodiscs decrease. In some embodiments, there is an asymptotic value for the relative amount of the polymer or copolymer above which there is no further substantial decrease in the size/diameter of the nanodisc.

The formation of the polymer- or copolymer-based lipid nanodiscs of the disclosure can be confirmed and characterized using a number of well-known techniques such as static light scattering (SLS), dynamic light scattering (DLS), size-exclusion chromatography (SEC), Fourier-transform infrared spectroscopy (FT-IR), solid-state nuclear magnetic resonance (ssNMR), and transmission electron microscopy (TEM). Advantageously, when the nanodiscs are less than or equal to about 40 nm, the structure of the nanodiscs can be determined based on solution NMR techniques and when the nanodiscs are greater than about 40 nm, the nanodiscs can be magnetically-aligned which is advantageous for solid-state NMR studies. Furthermore, as the polymers or copolymers of the disclosure can be free of styrene and/or aromatic groups, the nanodiscs can be characterized using biophysical techniques such as circular dichroism (CD), ultraviolet-visible spectroscopy (UV/Vis), and fluorescence spectroscopy.

Method of Characterizing Membrane Proteins

The disclosure further provides a method of characterizing a membrane protein, the method including contacting a lipid nanodisc of the disclosure with a membrane protein to form a membrane protein-nanodisc including the membrane protein spanning across the lipid bilayer from the first hydrophilic face, to the second hydrophilic face of the lipid nanodisc and characterizing the lipid nanodisc including the membrane protein. In some embodiments, the membrane protein spans across the entire lipid bilayer from the first hydrophilic face to the second hydrophilic face more than once. The membrane protein can be any membrane protein disclosed herein. In some embodiments, the membrane protein spans across half of the lipid bilayer from one hydrophilic face to the center of the hydrophobic edge.

In some embodiments, the contact includes admixing the lipid nanodisc and membrane protein in solution. In some embodiments, the solution is substantially free of detergent.

Characterization can include at least one of a structural characterization of the membrane protein or a functional characterization of the membrane protein. Suitable membrane protein characterization methods include solution and solid state nuclear magnetic resonance (NMR), circular dichroism (CD), electron paramagnetic resonance (EPR), Fourier transform infrared spectroscopy (FTIR), resonance Raman spectroscopy, ultraviolet-visible spectroscopy (UV/vis), cryo-electron microscopy (cryo-EM), surface plasmon Raman spectroscopy, sum frequency generation (SFG), fluorescence, including single molecule fluorescence and coherent anti-Stokes Raman (CARS), small angle x-ray scattering (SAXS), scanning electron microscopy (SEM), atomic force microscopy (AFM) and enzymatic assays Membrane protein structure and dynamics can be characterized using NMR techniques. For example, membrane protein-nanodiscs having a diameter of about 40 nm or less can be characterized using solution NMR and membrane protein-nanodiscs having a diameter greater than about 40 nm can be characterized using solid state NMR. Advantageously, the nanodiscs of the disclosure can include additional features for enhancing characterization by NMR, for example, the nanodisc can be characterized in that when a magnetic field is applied, the nanodisc aligns with the magnetic field and the nanodisc optionally includes a chelating group having a metal ion bound thereto as part of the pendant or backbone hydrophilic group which allows paramagnetic resonance characterization.

Magnetically aligned nanodiscs provide a novel membrane mimetic environment for the structural investigation of several membrane proteins by measuring $^1$H-$^{15}$N heteronuclear dipolar couplings. One of the most popular approaches to measure heteronuclear dipolar couplings in ssNMR is the 2D separation of heteronuclear dipolar interactions according to chemical shifts. This class of experiments is known as Separated Local Field (SLF) spectroscopy. Polarization Inversion and Spin Exchange at Magic Angle (PISEMA) is a well-known and useful NMR technique for structural studies of a variety of biological systems.

The modified polyacrylic acid polymer-based and copolymer-based lipid nanodiscs of the disclosure can be advantageous for one or more applications including, reconstitution of membrane proteins, purification of membrane proteins or peptides, drug delivery, and controlling the aggregation of amyloid peptides or proteins.

The above described aspects and embodiments can be better understood in light of the following examples, which are merely intended to be illustrative and are not meant to limit the scope in any way.

EXAMPLES

Example 1: Preparation of Copolymer

A polymethacrylate copolymer was prepared via free radical polymerization initiated by azobisisobutyronitrile (AIBN) according to the following reaction scheme:

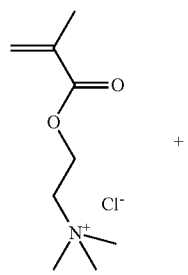

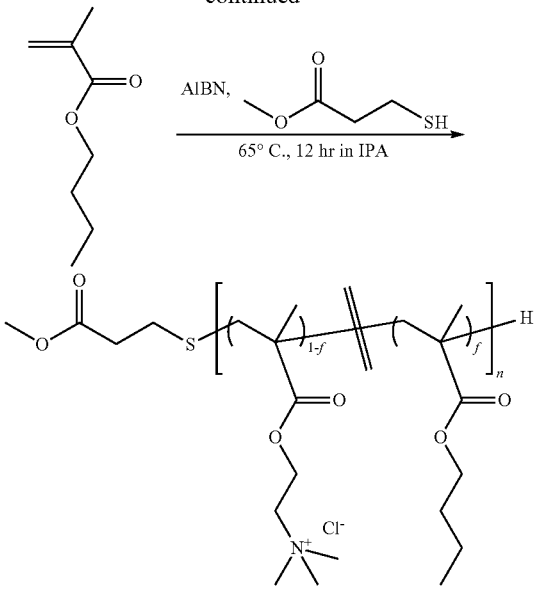

In particular, 0.2 mmol of methacroylcholine chloride supplied by TCI Co., Ltd. (Tokyo, Japan), 100 µL of AIBN in isopropyl alcohol (8.21 mg/mL, 5 µmol, 1 mol % total monomers), and 100 µL of 3-mercaptopropionate (MMP) in isopropyl alcohol (30.04 mg/mL, 25 µmol, 5 mol % total monomers) were dissolved in 300 µL isopropyl alcohol. The solution was bubbled with nitrogen gas for 5 minutes to remove any dissolved oxygen. To the solution, 0.3 mmol of butyl methacrylate supplied by TCI Co., Ltd. (Tokyo, Japan) was added. The solution was stirred at 65° C. overnight, after which the isopropyl alcohol solvent was removed in vacuo and the copolymer was dissolved in approximately 300 µL of methanol. The resultant copolymer solution was added to ice cold diethyl ether to induce precipitation of the copolymer. The resultant precipitate was collected via centrifugation and lyophilized from aqueous solutions to give a copolymer in the form of a white powder. The copolymer was stored at room temperature until use.

Figure 2:
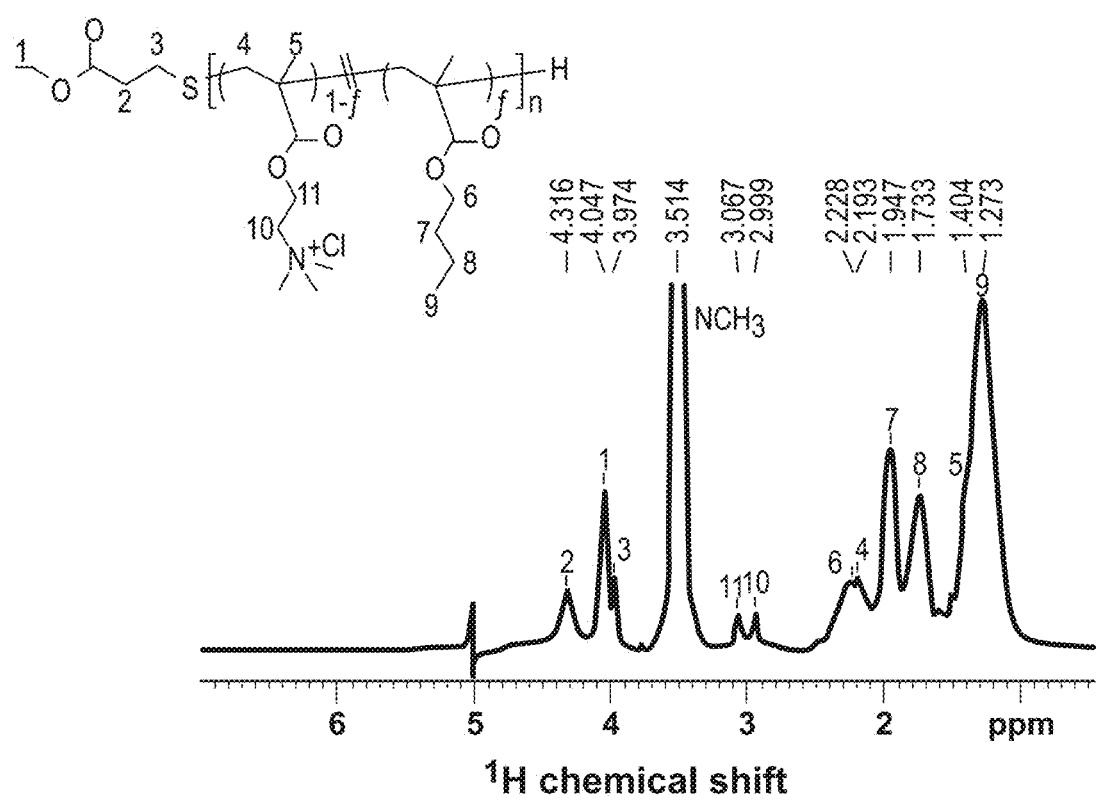
FIG. 2 shows a sample $^1$H NMR spectrum of a copolymer according to the disclosure.

The resultant copolymer was characterized via $^1$H NMR analysis to determine the degree of polymerization (DP), the number-average molecular weight ($M_n$), and the mole fraction of butyl methacrylate, f, of the copolymer. The spectrum was obtained at 25° C. by dissolving 2 mg of the copolymer sample in 600 µL of 100% $D_2O$ to provide a final concentration of 0.8 mM. The integration of signals from the following chemical groups was used for the characterization of the copolymer: methoxy terminal of the polymethacrylate backbone ($CH_3OCO$, 4.0 ppm, 3H), methylene group in choline side chains (($CH_3)_3N^+CH_2$, 2.9 ppm, 2H), and the methylene in both monomeric units ($COOCH_2$, 2.2 ppm, 2H). A representative spectrum for a copolymer according to the disclosure having a hydrophobicity of 0.60 and a number-average molecular weight of 4.7 kg/mol is demonstrated in FIG. 2.

Additional copolymers having various hydrophobicity fractions and molecular weights were prepared by varying the amount of MMP and the feed ratios of the methacroylcholine chloride and butyl methacrylate monomers.

Thus, Example 1 demonstrates the preparation of an acryloyl-based copolymer according to the disclosure.

Example 2: Preparation and Analysis of Copolymer-Based Lipid Nanodiscs

Large unilamellar vesicles (LUVs) having a diameter of 100 nm were prepared by dissolving 10 mg of 1,2-dimyristoyl-sn-glycero-3-phosphocholine (DMPC) from Avanti Polar Lipids, Inc. (Alabaster, Ala., USA) in 1 mL of chloroform. The solvent was evaporated under a stream of nitrogen gas and the residual trace solvent was completely removed in vacuo for three hours to provide a thin lipid film on the wall of a glass vial. The resultant lipid film was then hydrated by vertex mixing with 10 mM HEPES buffer (pH=7.4, 150 mM NaCl) at 40° C. To homogenize the size of LUVs, the liposome dispersion was subjected to five freeze-and-thaw cycles at −196° C. and 50° C., followed by extrusion (11 times) through stacked 100 nm polycarbonate membrane filters installed in the LIPOSOFAST miniextruder from Avestin.

The solubilization of the vesicles in solutions of the copolymers of Example 1 was determined by adding 2 µL of a dimethyl sulfoxide (DMSO) stock solution of the copolymer to 198 µL of the hydrated vesicle solution and mixing using a mechanical pipette. The final concentration of the phospholipids in the copolymer-vesicle mixture was set to 100 µM and incubated for 30 minutes at room temperature prior to measurement. The addition of the copolymers from Example 1 to the DMPC vesicles resulted in a decrease of the solution turbidity, reflecting the copolymer-induced fragmentation of vesicles and resulting lipid nanodisc formation, as shown in FIG. 3 panel A.

To further examine the effects of copolymer concentration, hydrophobicity, and molecular weight of the copolymer on vesicle fragmentation, the scattering intensity or turbidity was monitored by varying the copolymer:lipid ratio. Light scattering and hydrodynamic diameter of nanodiscs were measured using a dynamic light scattering spectrometer equipped with a laser diode illuminating at 665 nm (ELS-Z1000ZS, Otsuka Electronics Co., Ltd., Osaka, Japan). Size distribution of nanodiscs in an aqueous solution was obtained by analyzing a time course of scattered light intensity at an angle of 165° from the incident light with the Contin method. The sample temperature was maintained at 25° C. by the thermostat temperature controller installed in the equipment. The sample dispersion was filtrated using commercially available hydrophilic syringe filter with 450 nm pores to remove any dust from the sample prior to measurement.

Figure 3C:
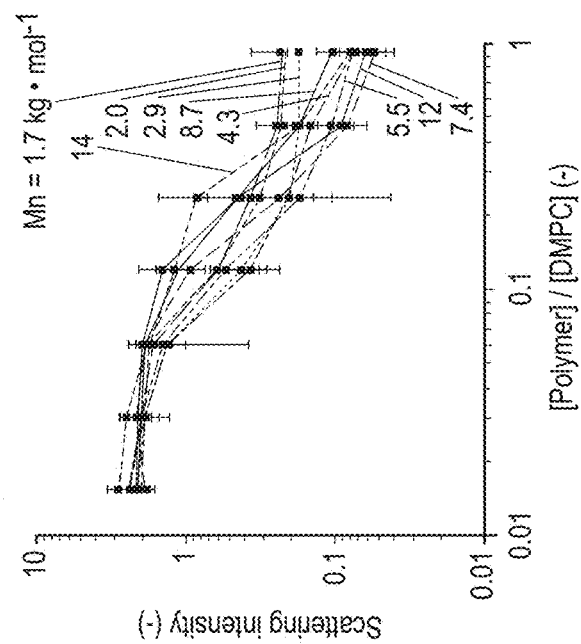
FIG. 3C shows the effect of the molecular weight of a copolymer on the copolymer-induced fragmentation of a DMPC lipid membrane.
Figure 3B:
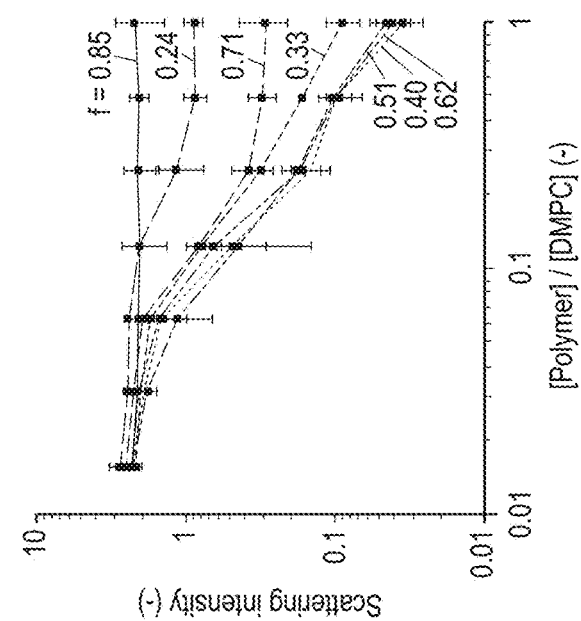
FIG. 3B shows the effect of the hydrophobicity of a copolymer on the copolymer-induced fragmentation of a DMPC lipid membrane.
Figure 3A:
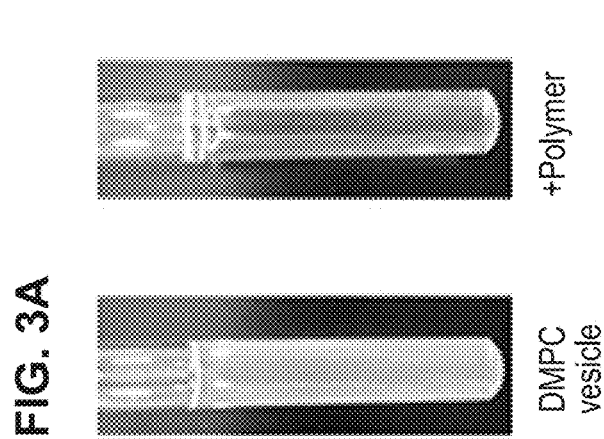
FIG. 3A shows the visual change in turbidity as a result of copolymer-induced fragmentation of a DMPC lipid membrane.
Figure 4A:
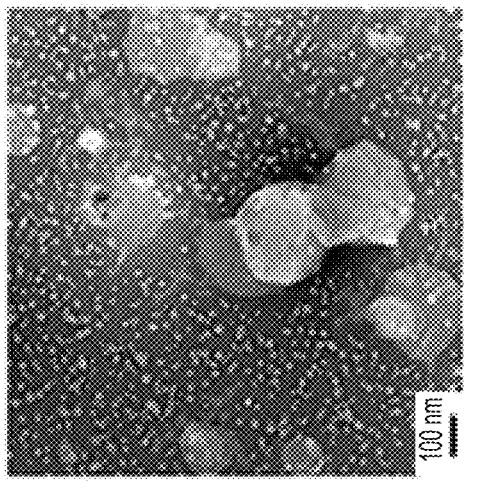
FIG. 4A shows the change in morphology of a copolymer-lipid complex via negative-stain TEM images of a copolymer-lipid complex when the copolymer has a hydrophobicity of 0.60 and a molecular weight of 4.7 kg/mol.
Figure 4B:
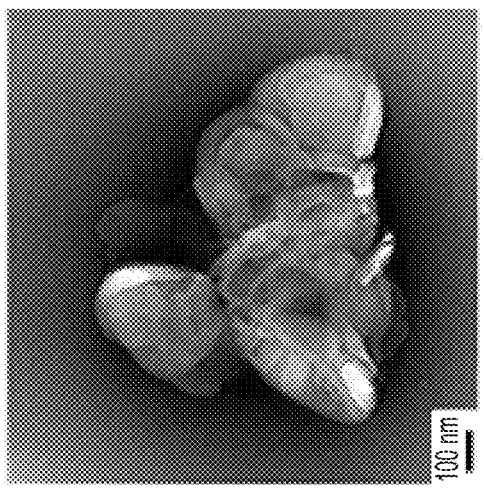
FIG. 4B shows the change in morphology of a copolymer-lipid complex via negative-stain TEM images of a copolymer-lipid complex when the copolymer has a hydrophobicity of 0.24 and a molecular weight of 6.1 kg/mol.
Figure 4C:
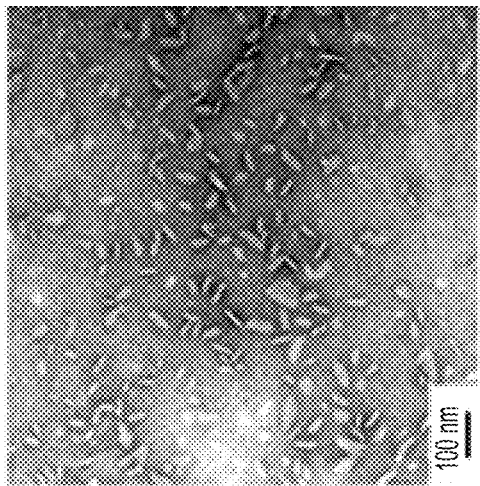
FIG. 4C shows the change in morphology of a copolymer-lipid complex via negative-stain TEM images of a copolymer-lipid complex when the copolymer has a hydrophobicity of 0.85 and a molecular weight of 6.1 kg/mol.
Figure 4D:
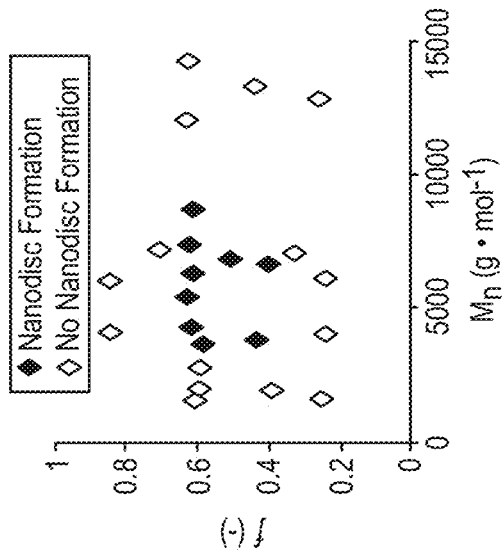
FIG. 4D shows the change in morphology of a copolymer-lipid complex via negative-stain TEM images of a copolymer-lipid complex when the copolymer has a hydrophobicity of 0.61 and a molecular weight of 1.7 kg/mol.
Figure 4E:
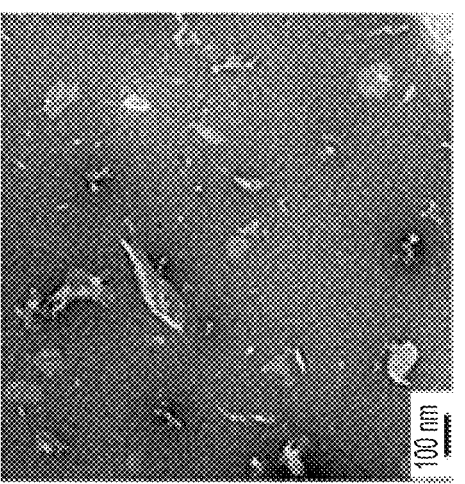
FIG. 4E shows the change in morphology of a copolymer-lipid complex via negative-stain TEM images of a copolymer-lipid complex when the copolymer has a hydrophobicity of 0.63 and a molecular weight of 14 kg/mol.
Figure 4F:
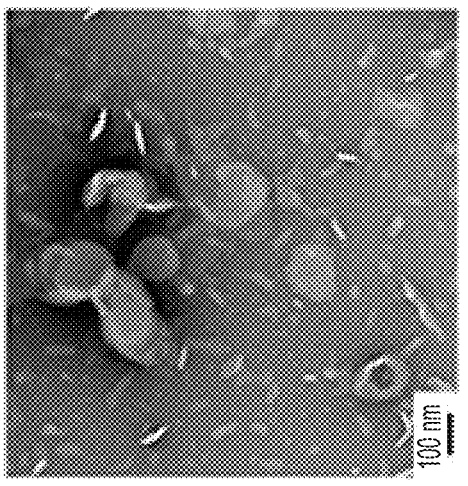
FIG. 4F shows the effect of the hydrophobicity and number average molecular weight of the copolymers on the formation of lipid nanodiscs.

As shown in FIG. 3 panel B, some polymers with moderate hydrophobicity fraction (f) of around 0.3 to 0.6 induced a significant decrease in the scattering light intensity with increasing copolymer concentration, reflecting the fragmentation of the vesicular membrane. In contrast, polymers having extreme hydrophobicity fractions, such as 0.85 or 0.24, were found to be ineffective in the solubilization of the vesicles. Further shown in FIG. 3 panel C, a copolymer with a relatively low molecular weight of around 3 kg/mol was ineffective in vesicle solubilization when compared to a large molecular weight copolymer, reflecting that a short copolymer cannot cover the hydrophobic thickness of the lipid bilayer.

Example 3: Morphology of Copolymer-Based Lipid Nanodisc

The morphology of the copolymer-lipid complex was examined by negative-stain transmission electron microscopy (TEM). Lipid nanodiscs formed from mixing the LUVs with polymers having differing hydrophobic fractions and molecular weights were analyzed by TEM to determine the polymers' effectiveness in inducing vesicle fragmentation and nanodisc formation.

As shown in FIG. 4 panel A, a copolymer having a hydrophobicity of 0.60 and a molecular weight of 4.7 kg/mol resulted in a homogeneous oval-shaped assembly of nanodiscs, reflecting the lipid bilayer nanodisc formation. Nanodiscs formed from polymers having very low hydrophobicity values (e.g., 0.24) and very high hydrophobicity values (e.g., 0.85), however, did not show effective or homogeneous fragmentation of the vesicles, as shown in FIG. 4, panels B and C, respectively.

Additionally, a copolymer with a low molecular weight (e.g., 1.7 kg/mol) was found to partially disrupt lipid vesicles, as confirmed from the formation of a vesicle/nanodisc mixture, as shown in FIG. 4, panel D. In contrast, a large molecular weight copolymer (e.g., 14 kg/mol) was found to form a heterogeneous mixture of small particles and large fragments of DMPC lipid vesicles, as shown in FIG. 4, panel E.

The effects of the hydrophobic fraction (f) and molecular weight ($M_n$) of the copolymer on the lipid nanodisc formation, based on the solubilization assay as well as TEM observation are summarized in FIG. 4, panel F. The solid-filled diamonds represent the ability of the polymers to form nanodiscs according to the disclosure.

The size, shape, and homogeneity of the lipid nanodiscs formed using the copolymers of the disclosure were further examined using cryo-TEM experiments. The cryo-TEM experiments confirmed that a 1:8 mixture of a copolymer having a hydrophobic fraction of 0.60 and a molecular weight of 4.7 kg/mol with the DMPC vesicles formed homogeneous nanodiscs, having a diameter of about 17 nm and a thickness of about 5.5 nm, which corresponded to the thickness of a single DMPC lipid bilayer.

Example 4: Fragmentation of Intact E. Coli Cells by Copolymer

The fragmentation of intact and live *Escherichia coli* cells using the polymers of the disclosure was analyzed using light scattering and TEM.

Figure 5A:
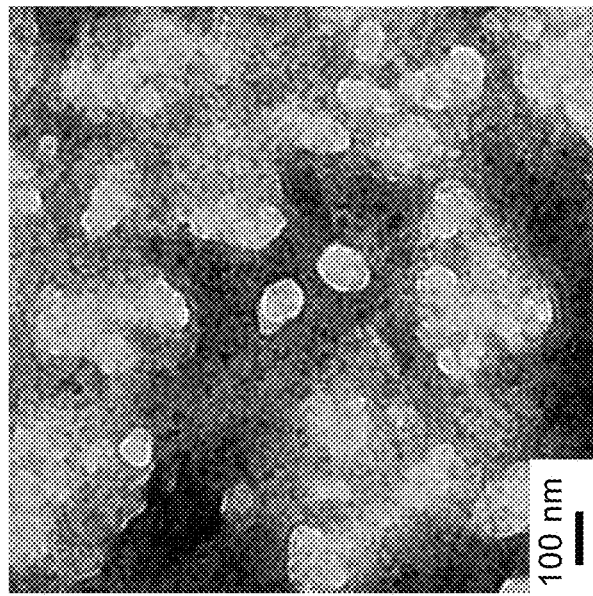
FIG. 5A shows the effect of a copolymer according to the disclosure on the scattering intensity of an *Escherichia coli* suspension.
Figure 5B:
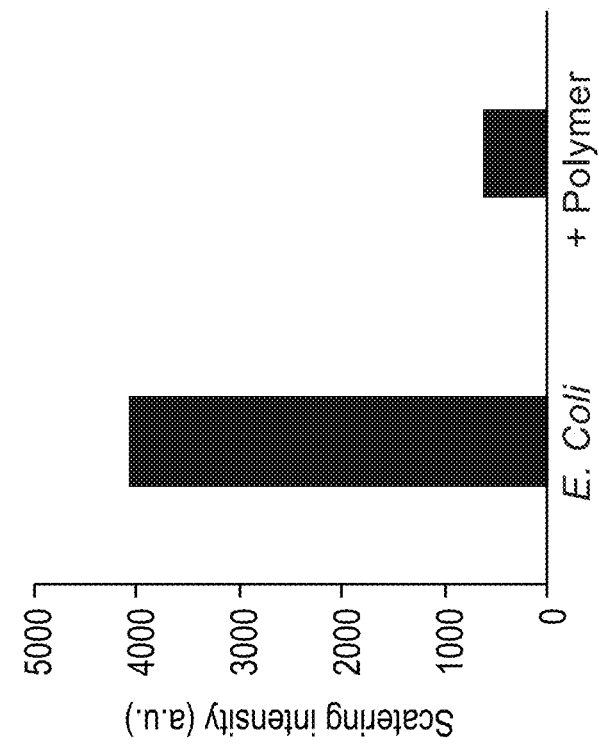
FIG. 5B shows a negative-stain TEM image of a copolymer-*E. coli* mixture.
Figure 6A:
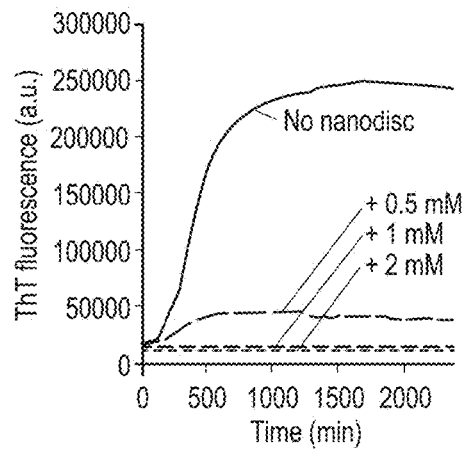
FIG. 6A shows a fluorescence spectrum for polymer nanodisc inhibition of human-IAPP (hIAPP) aggregation at hIAPP concentrations of 20 μM.
Figure 6C:
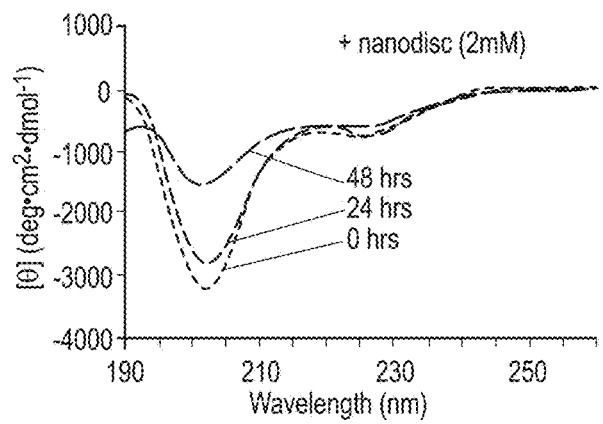
FIG. 6C shows a CD spectrum for polymer nanodisc inhibition of hIAPP aggregation at 20 μM hIAPP when in the presence of polymer nanodiscs according to the disclosure.
Figure 6B:
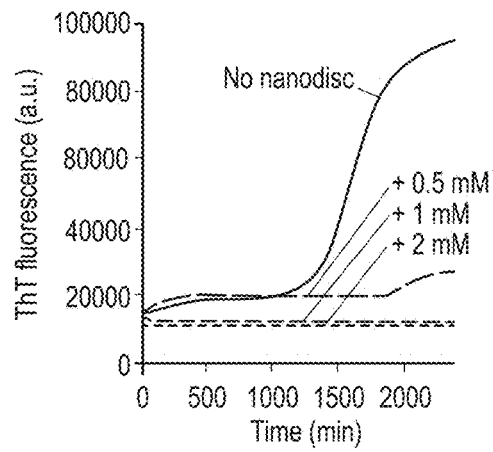
FIG. 6B shows a fluorescence spectrum for polymer nanodisc inhibition of human-IAPP (hIAPP) aggregation at hIAPP concentrations of 10 μM.
Figure 6D:
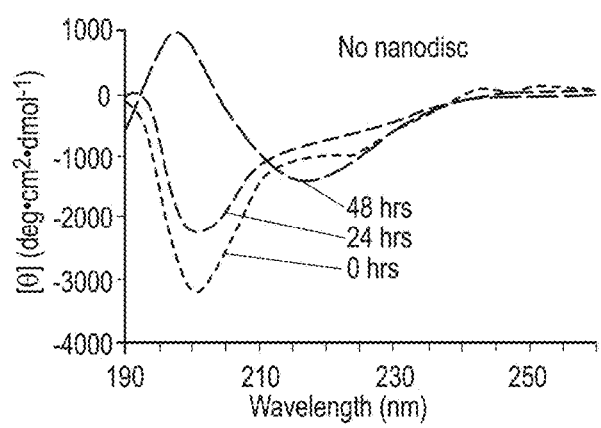
FIG. 6D shows a CD spectrum for polymer nanodisc inhibition of hIAPP aggregation at 20 μM hIAPP when in absence of polymer nanodiscs according to the disclosure.
Figure 7A:
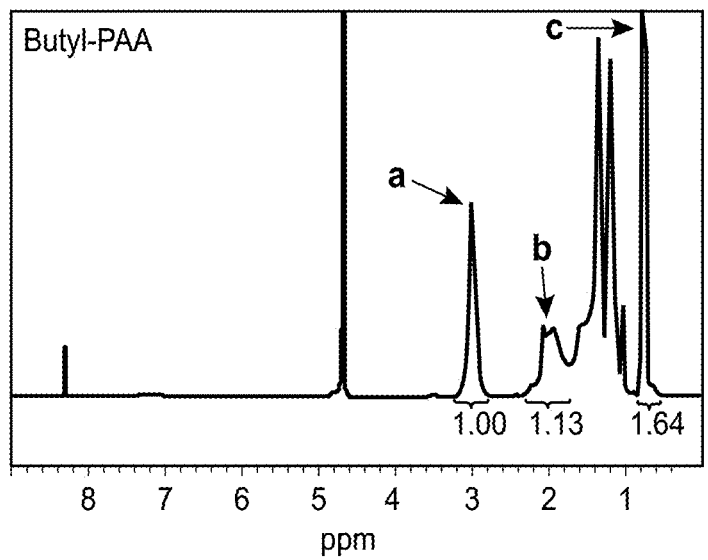
FIG. 7A shows a sample $^1$H NMR spectrum of a butyl-modified polyacrylic acid polymer.
Figure 7B:
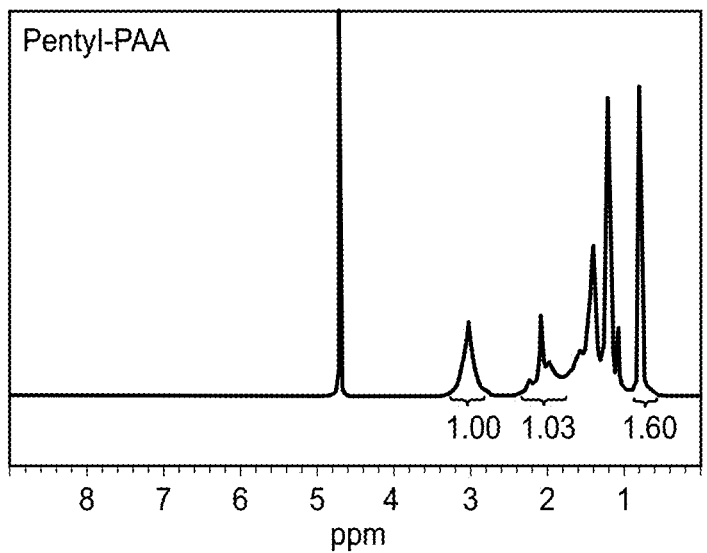
FIG. 7B shows a sample $^1$H NMR spectrum of a pentyl-modified polyacrylic acid.
Figure 7C:
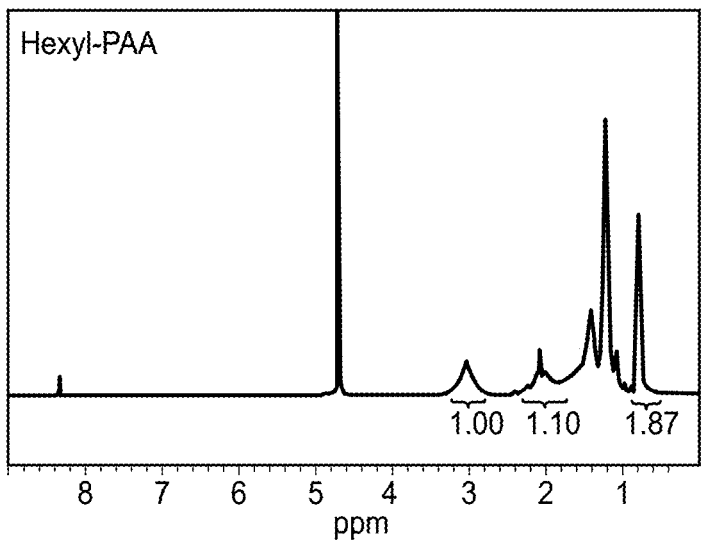
FIG. 7C shows a sample $^1$H NMR spectrum of a hexyl-modified polyacrylic acid.
Figure 7D:
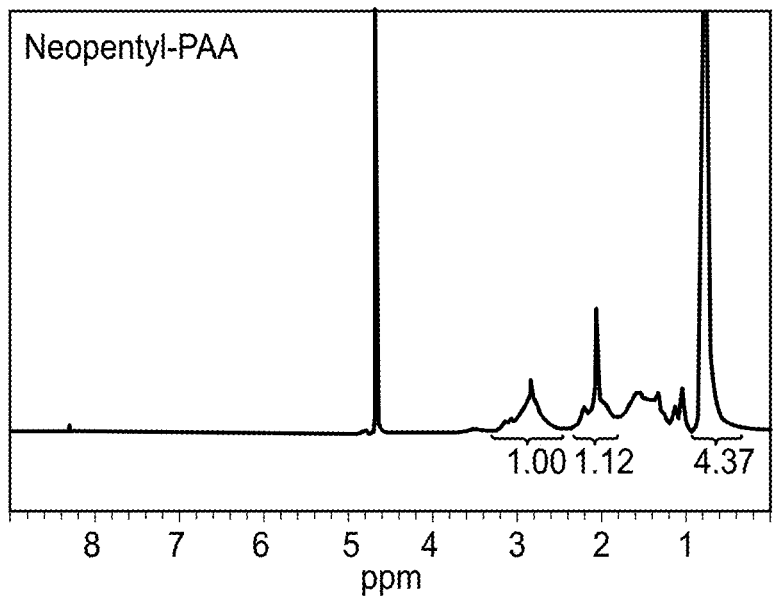
FIG. 7D shows a sample $^1$H NMR spectrum of a neopentyl-modified polyacrylic acid.
Figure 7E:
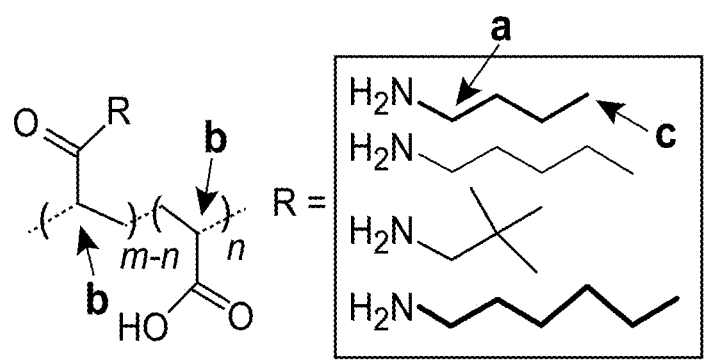
FIG. 7E shows the structure of the alkyl modification to the backbone of the polyacrylic acid polymer according to the disclosure and identifies hydrogens a-c labeled in FIG. 7A.

The addition of a copolymer having a hydrophobic fraction of 0.60 and a molecular weight of 4.7 kg/mol dramatically decreased the light scattering intensity of the *E. coli* suspension. As shown in FIG. 5, panels A and B, the addition of the copolymer of the *E. coli* suspension resulted in the formation of small particles, demonstrating the copolymer-induced disruption of the cells.

Thus, Example 4 demonstrates that the acryloyl-based nanodisc-forming copolymer of the disclosure is applicable not only to solubilized lipid vesicles, but also to intact cell membranes.

Example 5: Analysis of Amyloid Aggregation Using Nanodiscs

Thioflavin T (ThT)-based fluorescence and CD studies were performed to demonstrate the ability to measure the interactions of naturally-occurring C-amidated form of human islet amyloid polypeptide (hIAPP, also known as human amylin) and the lipid nanodiscs. Human amylin has been shown to play important role in insulin-producing islet death in type-2 diabetes.

A 9:1 molar ratio of DMPC:DMPG was dissolved in chloroform, dried under nitrogen gas, and the residual solvent was removed under high vacuum overnight. The resulting lipid film was rehydrated in 30 mM acetic acid buffer (pH 5.3) to make a 10 mg/ml stock solution of the lipid. A 450 µl aliquot of a 10 mg/ml in water solution of the copolymer was added to 300 µl lipid solution and incubated overnight. Excess copolymer was removed by washing with buffer using Amicon filter using a 30 kDa cutoff membrane. The resulting solution was used for experimental measurements reported in this study. All samples were prepared freshly before the start of each experiment.

The ThT fluorescence results obtained in the absence of nanodiscs and in the presence of 9:1 DMPC:DMPG copolymer nanodiscs for two different concentrations (10 and 20 µM) of hIAPP are shown in FIG. 6 panels A and B, respectively. In the absence of nanodiscs, the sigmoidal ThT traces suggest the time- and concentration-dependent aggregation of hIAPP to form amyloid fibers. In contrast, the addition of the nanodiscs significantly reduced and completely suppressed the ThT signal intensity. Accordingly, these results suggest the nanodiscs effectively suppressed the amyloid fiber formation of hIAPP.

Circular dichroism studies were performed to further confirm the suppression of fiber formation by the nanodiscs. As shown in FIG. 6 panel C, the hIAPP peptide forms a helical structure in the presence of nanodiscs, indicated by the negative minima at 209 and 220 nm in the CD spectrum. In contrast, as would be expected, in the absence of nanodiscs, the hIAPP peptide forms a beta-sheet structure, as shown in FIG. 6, panel D, indicated by the positive band at about 195 nm and the negative band at about 218 nm. It was also confirmed that the copolymer alone did not provide the stabilization of the helical structure seen with the lipid nanodisc of the disclosure.

Thus, Example 5 demonstrates the ability of the lipid nanodiscs of the disclosure to stabilize a helical intermediate of hIAPP. This unique application of the lipid nanodiscs is observable due to the lack of styrene and/or an aromatic group that can interfere with commonly used biophysical experiments such as CD and fluorescence.

Example 6: Preparation of Alkylated Poly(Acrylic Acid)

A modified poly(acrylic acid) polymer was prepared via a simple condensation reaction using poly(acrylic acid) (PAA), a coupling reagent and an alkyl amine according to the following reaction scheme:

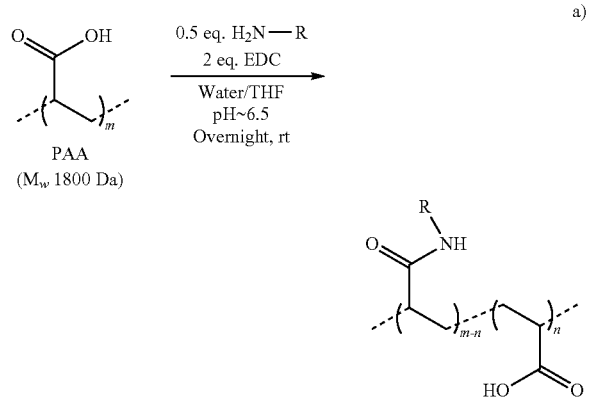

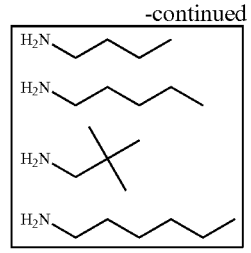

In particular, 4 g PAA (average $M_W$ 1800, 25 acrylic acid groups per chain) was dissolved in 160 mL tetrahydrofuran (THF). 2 eq. of (3-Dimethylaminopropyl)-N-ethylcarbodiimide hydrochloride (EDC) per acrylic acid group (22 g) was added to the solution and stirred. ddH$_2$O was added to the stirring solution until all the EDC was dissolved. 0.5 eq. of pentylamine per acrylic acid unit (2.42 g, 3.22 mL) was added to the reaction mixture and the pH was adjusted to about 6.5 if needed. The mixture was diluted with THF and water to yield a final ratio of 70:30 THF:Water solution. The final solution was stirred overnight at room temperature. After completion, THF was removed using rotary evaporation at 40° C. and the cloudy mixture was diluted with an excess 1M NaOH (100 mL) and heated to 80° C. and stirred for 2 hours to hydrolyze any potential anhydrides formed during the reaction. The clear solution was precipitated using 1M HCl, centrifuged at 3500 g, washed 3 times with ddH$_2$O and lyophilized until dry. The overall reaction yielded 4.5 g of final pentyl-PAA polymer.

The resultant modified polymer was characterized via $^1$H NMR analysis to confirm the successful completion of the coupling reaction and to estimate the extent of functionalization by integration. The spectrum was obtained at 25° C. by dissolving 4 mg of the modified polymer sample in 600 µL of 100% D$_2$O. The extent of functionalization was found to be about 40-50%, within the range of optimal hydrophobic to hydrophilic ratio of nanodiscs. Peak integration was done by setting the area of alpha CH$_2$ peak to 1.0. A representative spectrum for a modified PAA according to the disclosure having a hydrophobicity of 0.60 and a number-average molecular weight of 4.7 kg/mol is demonstrated in FIG. 7, wherein peaks labeled with a, b, and c belong to the alpha-CH$_2$, CH of the polymer backbone and CHs of the alkyl chain, respectively.

Additional modified polymers having various alkyl amines (e.g., butyl, hexyl, and neopentyl) were prepared by varying the alkyl amine and the $^1$H NMR spectra are also shown in FIG. 7.

Thus, Example 6 demonstrates the preparation of PAA polymers modified with alkyl amines according to the disclosure.

Example 7: Preparation and Analysis of Modified PAA Based Lipid Nanodiscs

Nanodiscs having hydrodynamic diameters in a range of 3 to 100 nm were prepared as follows. 10 mg of 1,2-dimyristoyl-sn-glycero-3-phosphocholine (DMPC) from Avanti Polar Lipids, Inc. (Alabaster, Ala., USA) was dissolved in 1 mL of chloroform. The solvent was evaporated under a stream of nitrogen gas and the residual trace solvent was completely removed in vacuo for three hours to provide a thin lipid film on the wall of a glass vial. The resultant lipid film was then hydrated by vertex mixing with potassium phosphate buffer (pH=7.41) to form multilamellar vesicles (MLV).

Alkyl-PAA stock solutions of 20 mg/mL were prepared by dissolving the polymers prepared according to Example 6 (pentyl-PAA, neopentyl-PAA, hexyl-PAA, butyl-PAA) with a minimum amount of 0.1 M NaOH and diluting to the necessary concentration using potassium phosphate buffer. The resulting stock solutions were then added together at various polymer:lipid weight ratios (0.25:1, 0.5:1, 1:1) and diluted to 1 mL using buffer. The resulting solutions were incubated at 35° C. overnight. Free polymer was removed either using SEC or centrifugation filtration using a 10 kDa filter.

While the pentyl-PAA, neopentyl-PAA, and hexyl-PAA were found to solubilize DMPC vesicles into small particles, the Butyl-PAA needed a much higher amount of polymer to achieve solubilization (>1:1). Solubilization was monitored using static light scattering.

Size exclusion chromatography and dynamic light scattering was used to determine the size distribution of the polymer nanodiscs. SEC chromatograms showed the presence of two peaks:nanodiscs eluted within the region of 9-12 mL whereas free polymer eluted at 15-20 mL. All three polymers, pentyl-PAA, neopentyl-PAA, and hexyl-PAA, showed size tunability by varying the polymer:lipid ratio, wherein smaller nanodiscs were formed at higher polymer:lipid ratios, as shown in FIG. 8.

The dynamic light scattering was performed using Wyatt Technology® DynaPro® NanoStar® using a 1 microliter quartz MicroCuvette, or equivalent. Size exclusion chromatorgraphy (SEC) used self-packed Superdex 200 Increase 300/10 GL column operated on an AKTA purifier (GE Healthcare, Freiburg, Germany), or equivalent. Samples were monitored at 214 nm.

Thus, Example 7 shows preparation and characterization of lipid nanodiscs of the disclosure having various sizes prepared by altering the polymer:lipid weight ratios.

Example 8: Effect of Magnetic Field on Modified PAA Polymer Nanodiscs

Figures 9A, 9B, 9C:
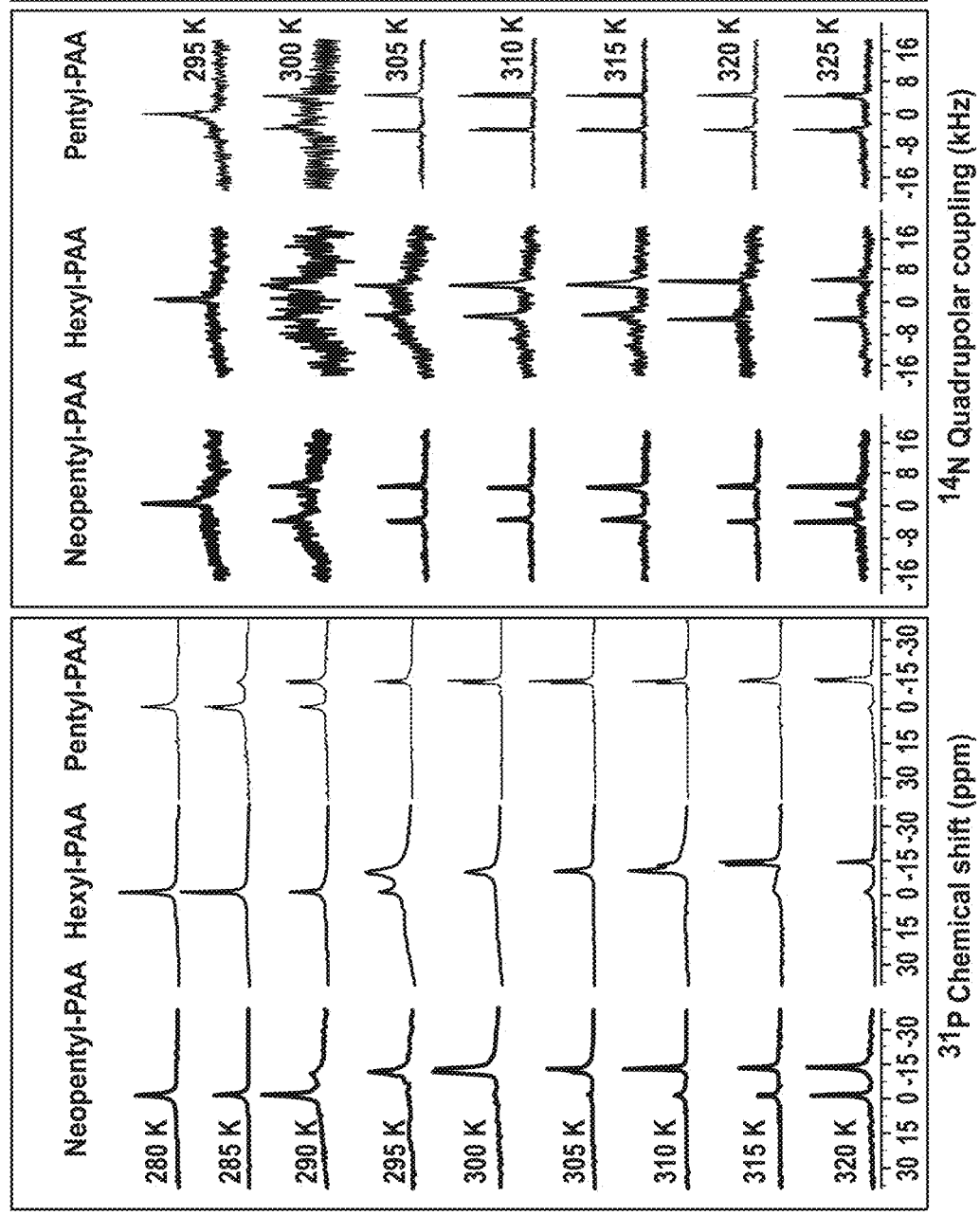
FIG. 9A shows a sample $^{31}$P spectrum of the nanodiscs of the disclosure prepared from neopentyl-, hexyl-, and pentyl-PAA.
FIG. 9B shows a sample $^{14}$N NMR spectrum of the nanodiscs of the disclosure prepared from neopentyl-, hexyl-, and pentyl-PAA.
FIG. 9C shows a schematic representation of the magnetic alignment of the nanodiscs.

Macro-nanodiscs were prepared to examine the ability of the nanodiscs to spontaneously align in the presence of a magnetic field. Nanodiscs were prepared using pentyl-PAA, hexyl-PAA, and neopentyl-PAA polymers as described in Example 6, using the lowest polymer:lipid ratio possible, and tested with $^{31}$P and $^{14}$N static solid state NMR experiments. The $^{31}$P NMR spectra were recorded at different temperatures ranging from 280 to 320K. $^{31}$P NMR showed the appearance and disappearance of two main peaks at about −1.5 ppm and in the region of about −12 to −14 ppm, as a function of temperature. The peak at about −1.5 ppm was due to the fast tumbling of isotropic nanodiscs, whereas the peak at −12 to −14 ppm was indicative of macro-nanodiscs with the lipid phosphate head groups aligned perpendicular to the magnetic field axis. Pentyl-PAA macro-nanodiscs showed an isotropic peak) about −1.5 ppm) at 280 K. Partial alignment of the nanodiscs was seen (about −12 ppm) at 285-290 K, and complete alignment above 295 K. Hexyl-PAA macro-nanodiscs showed alignment similar to pentyl-PAA macro-nanodiscs, however, they required a higher temperature (300K) to fully align, and at 320 K a small isotropic peak was observed. Neopentyl-PAA macro-nanodiscs had similar characteristics of pentyl-PAA nanodiscs at lower temperatures (<310 K) above which a large isotropic signal was observed, suggesting less stability at higher temperature as compared to pentyl-PAA. Similar trends were observed using $^{14}$N NMR. Representative NMR spectra a shown in FIG. 9.

$^{31}$P NMR spectra were acquired using An Agilent/Varian 400 MHz solid-state NMR spectrometer and a 5 mm triple-resonance probe with $^{31}$P and $^{1}$H resonance frequencies of 161.974 MHz and 400.114 MHz, respectively, or equivalent. 200 μl of sample was inserted using a 3.2 mm glass tube. 5 μs 90° pulse, 25 kHz $^{1}$H continuous-wave decoupling, 1024 scans, and a 2 s recycle delay were used to acquire $^{31}$P NMR spectra. $^{31}$P chemical shifts were referenced by setting the $^{31}$P chemical shift of 100% $H_3PO_4$ sample to 0 ppm.

$^{14}$N NMR spectra were acquired Agilent/Varian 400 MHz solid-state NMR spectrometer and a 5 mm double-resonance probe operating at the $^{14}$N resonance frequency of 29.910 MHz, or equivalent. $^{14}$N-NMR spectra were recorded using the quadrupole-echo pulse sequence with a 90° pulse length of 8 μs and an echo-delay of 80 μs. $^{14}$N magnetization was acquired using 28.9 ms acquisition time (without $^{1}$H decoupling), 20,000 scans and a recycle delay of 0.9 s.

Thus, Example 8 demonstrates that lipid nanodiscs of the disclosure can be aligned by magnetic field.

Example 9: Direct Membrane Protein Extraction from Cellular Membranes Using Modified-PAA Based Lipid Nanodiscs The modified PAA polymers were used for direct membrane protein extraction from cellular membranes by incubating the polymers with cell lysate following a published protocol, Lee et al. *Nat. Protoc.* 2016, 11, 1149.

In general, *E. coli* BL21 (DE3) was obtained as described in Prade et al. *Ange. Chem. Int. Ed.* 2018, 57, 8458. Cell pellets were re-suspended in a 10-fold volume of ice-cold buffer (50 mM potassium phosphate buffer, 2 mM EDTA, 200 mM NaCl, pH 7.4) and subjected to ultrasonication. The cell lysate was subjected centrifugation for 1 h at 4° C. and 20,000 g and washed three times with buffer to remove soluble proteins. Membrane pellets were re-suspended in 50 mM potassium phosphate buffer, 200 mM NaCl, pH 7.4 to a final concentration of 50 mg/mL. Solubilization of the pellet was conducted by treating 500 μl of cell lysate with 250 μl of modified PAA polymer solution (50 mg/mL). The samples were incubated overnight at room temperature while shaking. The resulting solutions were centrifuged at 11,000 g for 30 min. The supernatant was separated and analyzed using SDS PAGE gel. To remove the polymer and lipids, proteins were precipitated from polymer-containing samples with $CH_3OH/CHCl_3/H_2O$. 100 μL aliquot of ice-cold supernatant was mixed with 400 μL ice-cold methanol, then 100 μL ice-cold chloroform was added, and the sample was mixed. 300 μL ice-cold water was then added and the sample was thoroughly mixed and centrifuged at 2,000 g for 5 mins and 11,000 g for 10 mins at 4° C. The top aqueous layer was carefully removed and 400 μL of ice cold methanol was added and mixed thoroughly. The resulting precipitate was pelleted at 2,000 g for 5 mins and 11,000 g for 10 mins at 4° C. The resulting pellet was washed two times with 800 μL of ice cold methanol. Resulting pellet was dried under $N_2$ for 10 minutes and then under high vacuum for 3 hrs. The dry pellet was suspended in SDS buffer, heated to 100° C. for 10 mins with shaking and subjected to a SDS-PAGE.

Samples from above were loaded onto a precast gel. A constant voltage of 170 V was applied for 40 min at 50 W. Gels were fixed in 10% (v/v) acetic acid and 40% (v/v) ethanol, stained with 0.025% (w/v) Coomassie brilliant blue in 10% (v/v) acetic acid, and de-stained with 10% (v/v) acetic acid. Finally, gels were photographed using slandered digital camera.

Figure 10:
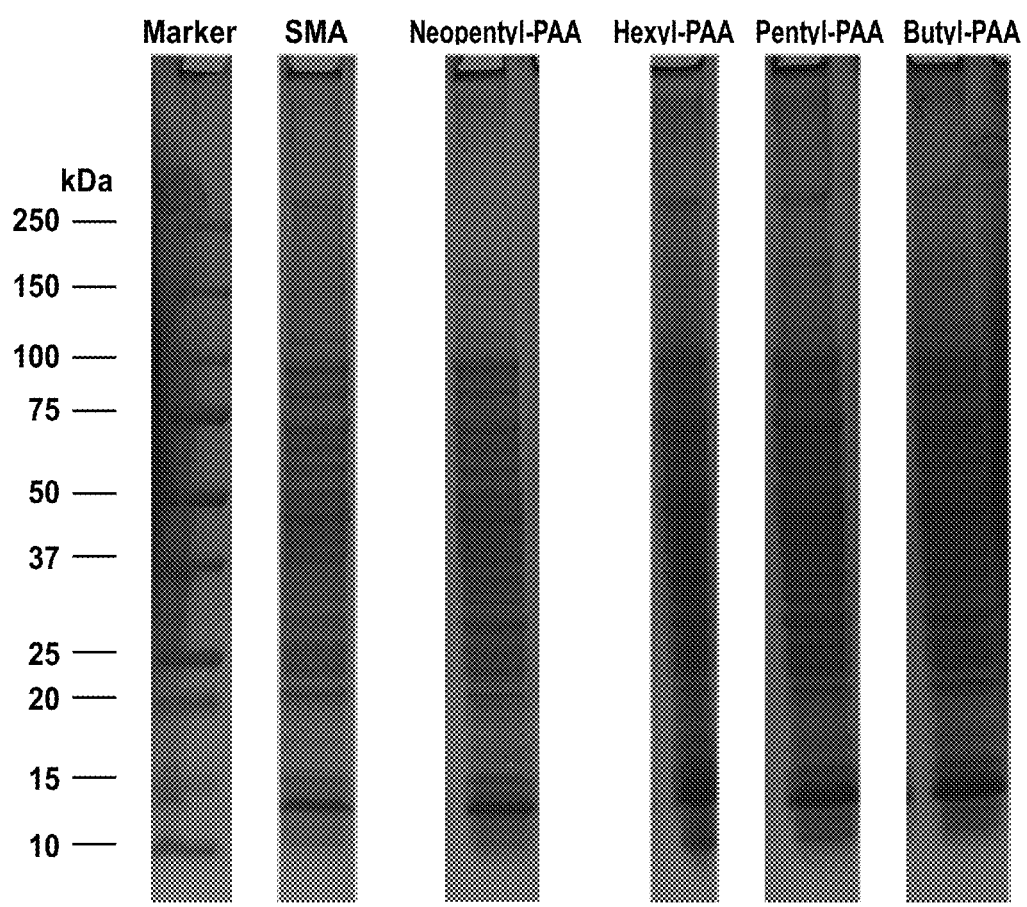
FIG. 10 shows an SDS-page gel of the extraction of various membrane proteins using different modified polyacrylic acid polymers.

All three PAA polymers showed similar efficacy as compared to styrene maleic acid lipid particles (SMALP) as evident from the SDS-PAGE gel, as shown in FIG. 10.

Thus, Example 9 shows that the modified PAA of the disclosure have the ability to extract membrane proteins from their native environment.

Example 10: Preparation of Modified PAA Including a Hydrophilic and Hydrophobic Pendant Group A pendant hydrophobic group was added to a pentyl modified poly(acrylic acid) polymer via a simple condensation reaction using pentyl modified poly(acrylic acid) (PAA), a coupling reagent and an amine according to the following reaction scheme:

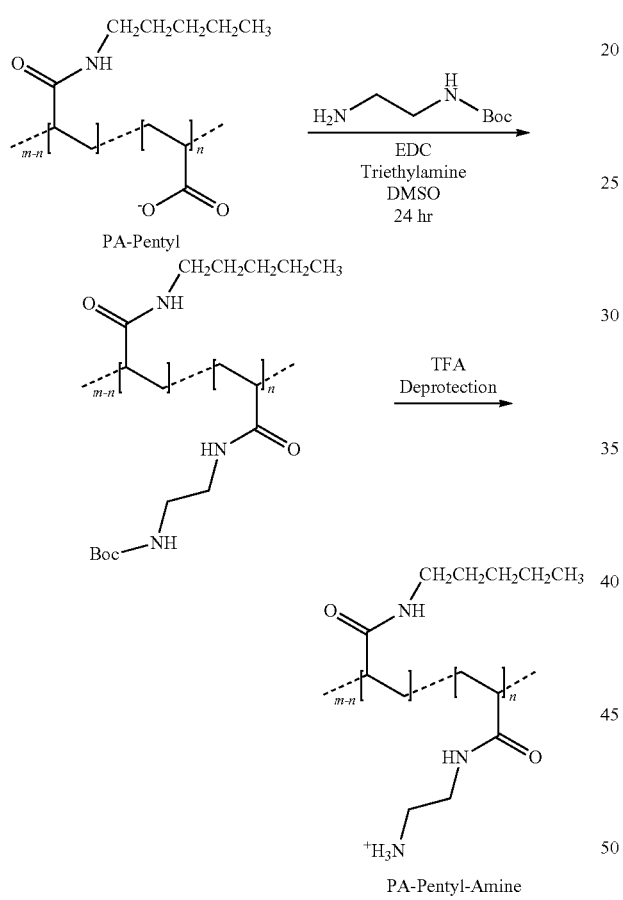

In particular, polyacrylic acid (1 g) having a molecular weight of 1800 g/mol (25 COOH per chain, on average) was dissolved in 40 mL dry DMSO. N-Boc-Ethylenediamine (1.12 ml) and pentyl amine (0.803 mL) (~12.5 eq of each) were predissolved in 10 mL dry DMSO and added. EDC (5.38 g, ~50 eq, or 2 eq per COOH) was added, and the reaction was stirred for 24 hours. Then 200 mL ddH$_2$O was added, and the reaction was extracted three times with 50 mL ethyl acetate. The organic layer was dried and filtered over sodium sulfate, and the ethyl acetate was removed with vacuum. The product was then deprotected by dissolving in 30 mL TFA and 10 drops of water and stirred for 2 hours. The final product was obtained after ether precipitation, washing, and drying under vacuum.

The resultant modified polymer was a low pH-resistant polymer (e.g., about pH 3 to about pH 8) that was also resistant to divalent metal cations. Further, nanodiscs having hydrodynamic diameters in a range of about 9 to about 20 nm were prepared using the PA-pentyl-amine polymers and 1,2-dimyristoyl-sn-glycero-3-phosphocholine (DMPC) as described in Example 7

Thus, Example 10 demonstrates the preparation of PAA polymers modified with a hydrophobic pendant group and a hydrophilic pendant group according to the disclosure. Example 10 further demonstrates the use of a PAA polymer modified with a hydrophobic pendant group and a hydrophilic pendant groups according to the disclosure in the preparation of a lipid nanodisc.

Example 11: Lipid Nanodisc Containing Drug

Benzylpenicillin was loaded into nanodiscs of the disclosure as follows. Benzylpenicillin sodium salt was converted to the acid form by dissolving 1 g of benzylpenicillin sodium salt in 27 mL water and 3 mL of 1M HCl in slight molar excess (93 mM benzylpenicillin to 100 mM HCl) Immediately, the mixture was vortexed and flash frozen using liquid nitrogen and lyophilized to give benzylpenicillin in its acid form. The acid form of the benzylpenicillin was added to DMPC and nanodiscs were prepared as described in Example 7. The benzylpenicillin containing nanodiscs were analyzed using $^1$H NMR and compared to the $^1$H NMR spectrum of free benzylpenicillin (sodium salt). The $^1$H NMR spectrum of the benzylpenicillin containing nanodiscs demonstrated clear broadening and shifting of the benzylpenicillin peaks relative to the free sodium salt, indicating reduced mobility and tumbling speed of the benzylpenicillan, confirming that the benzylpenicillin was inside the bilayer of the nanodiscs.

Thus Example 11 demonstrates the use of the lipid nanodiscs of the disclosure as drug-carriers.

What is claimed:

1. A lipid nanodisc comprising:
a lipid bilayer comprising a first hydrophilic face and a second hydrophilic face opposing the first hydrophilic face, and a hydrophobic edge between the opposing hydrophilic faces;
and a polymer encircling the hydrophobic edge of the lipid bilayer, wherein the polymer comprises a first monomeric unit comprising a pendant hydrophobic group and a second monomeric unit having a backbone hydrophilic group,
wherein the first monomeric unit has a structure according to Formula 3 or Formula 4:

$$—CR_3(C(=O)—N—R_4R_5)CR_1R_2— \qquad (3)$$

$$—CR_3(C(=O)—O—R_4)CR_1R_2— \qquad (4)$$

wherein:
each of $R_1$, $R_2$, $R_3$, and $R_5$ is independently selected from H and $C_{1-6}$ alkyl; and
$R_4$ is the pendant hydrophobic group selected from a linear $C_{4-14}$ alkyl group, a branched $C_{4-14}$ alkyl group, a cyclic $C_{4-14}$ alkyl group, or any combination thereof and
wherein the second monomeric unit has a structure according to Formula 5:

$$—CR_3(C(=O)—O—R_6)CR_1R_2— \qquad (5)$$

wherein:
each of $R_1$, $R_2$, and $R_3$ is independently selected from H and $C_{1-6}$ alkyl, and $R_6$ is H.

2. The lipid nanodisc of claim 1, wherein the first monomeric unit has a structure according to Formula 3.

3. The lipid nanodisc of claim 1, wherein the first monomeric unit is has a structure according to Formula 4.

4. The lipid nanodisc of claim 1, wherein the first monomeric unit is present in the polymer at a mole fraction of about 0.20 to about 0.90, based on the total amount of first and second monomeric units.

5. The lipid nanodisc of claim 1, wherein the first monomeric unit is present in the polymer at a mole fraction of about 0.24 to about 0.85, based on the total amount of first and second monomeric units.

6. The lipid nanodisc of claim 1, wherein the first monomeric unit is present in the polymer at a mole fraction of about 0.4 to about 0.6, based on the total amount of first and second monomeric units.

7. The lipid nanodisc of claim 1, wherein the polymer has a number-average molecular weight (Mn) from about 2.5 kg/mol to about 10 kg/mol.

8. The lipid nanodisc of claim 1, wherein the polymer is a random copolymer.

9. The lipid nanodisc of claim 1, wherein the lipid comprises at least one of phosphatidylethanolamines, phosphatidylcholines, phosphatidylglycerols, phosphatidylserines, cholesterols, sphingomyelin, gangliosides, phosphatidylinositols, lipopolysaccharides, and derivatives of the foregoing.

10. The lipid nanodisc of claim 1, wherein the lipid comprises a natural cell membrane extract.

11. The lipid nanodisc of claim 1, wherein the nanodisc has a diameter in a range of about 6 nm to about 100 nm.

12. The lipid nanodisc of claim 1, wherein the nanodisc has a diameter less than or equal to 40 nm.

13. The lipid nanodisc of claim 1, wherein the nanodisc has a diameter greater than 40 nm.

14. The lipid nanodisc of claim 1, wherein the nanodisc has a diameter in a range of about 50 nm to about 70 nm.

15. The lipid nanodisc of claim 1, further comprising a membrane protein spanning across the lipid bilayer from the first hydrophilic face to the second hydrophilic face.

16. The lipid nanodisc of claim 1, characterized in that when a magnetic field is applied, the nanodisc aligns with the magnetic field.

17. The lipid nanodisc of claim 1, wherein the polymer comprises a modified polyacrylic acid polymer encircling the hydrophobic edge of the lipid bilayer, wherein the modified polyacrylic acid comprises a backbone hydrophilic group and a pendant hydrophobic group.

18. The lipid nanodisc of claim 1, wherein the polymer is free of styrene.

19. The lipid nanodisc of claim 1, wherein the polymer is free of aromatic groups.

20. The lipid nanodisc of claim 1, wherein the lipid nanodisc further includes a drug.

21. A method of making a lipid nanodisc according to claim 1, the method comprising contacting a lipid and the polymer comprising a first monomeric unit having a pendant hydrophobic group and a second monomeric unit having a backbone hydrophilic group to form the lipid nanodisc.

22. A method of making a lipid nanodisc according to claim 1, the method comprising:
modifying a polyacrylic acid polymer to include a pendant hydrophobic group, wherein said modifying comprises admixing a polyacrylic acid polymer with a compound comprising a hydrophobic group and a functional group capable of coupling with polyacrylic acid, thereby forming a modified polyacrylic acid comprising a hydrophilic group and a pendant hydrophobic group; and,
contacting a lipid with the modified polyacrylic acid polymer to form a lipid nanodisc, said lipid nanodisc comprising a lipid bilayer comprising a first hydrophilic face and a second hydrophilic face opposing the first hydrophilic face, and a hydrophobic edge between the opposing hydrophilic faces and the polymer encircling the hydrophobic edge of the lipid bilayer.

23. A method of characterizing a membrane protein, the method comprising:
contacting the lipid nanodisc of claim 1 with a membrane protein to form a membrane protein-nanodisc comprising the membrane protein spanning across the lipid bilayer from the first hydrophilic face to the second hydrophilic face; and,
characterizing the lipid nanodisc comprising the membrane protein.

24. The method of claim 23, wherein the contacting comprises admixing the lipid nanodisc and membrane protein in solution.

* * * * *

UNITED STATES PATENT AND TRADEMARK OFFICE
CERTIFICATE OF CORRECTION

| | |
|---|---|
| PATENT NO. | : 11,813,358 B2 |
| APPLICATION NO. | : 16/893772 |
| DATED | : November 14, 2023 |
| INVENTOR(S) | : Ayyalusamy Ramamoorthy et al. |

It is certified that error appears in the above-identified patent and that said Letters Patent is hereby corrected as shown below:

In the Claims

At Column 28, Line 45, "and" should be at Line 44, after "hydrophilic faces;", as a continuation point.

At Column 28, Lines 62-63, "thereof and" should be -- thereof, and --.

At Column 29, Line 7, "is has" should be -- has --.

At Column 29, Line 21, "(Mn)" should be -- ($M_n$) --.

Signed and Sealed this
Twenty-second Day of October, 2024

Katherine Kelly Vidal
*Director of the United States Patent and Trademark Office*